US011104963B2

(12) United States Patent
Tyler

(10) Patent No.: US 11,104,963 B2
(45) Date of Patent: Aug. 31, 2021

(54) DETECTION OF SHIGA TOXIN GENES IN BACTERIA

(71) Applicant: GEN-PROBE PRODESSE, INC., San Diego, CA (US)

(72) Inventor: Ejan Tyler, San Diego, CA (US)

(73) Assignee: Gen-Probe Prodesse, Inc., San Diego, CA (US)

( * ) Notice: Subject to any disclaimer, the term of this patent is extended or adjusted under 35 U.S.C. 154(b) by 826 days.

(21) Appl. No.: 14/579,999

(22) Filed: Dec. 22, 2014

(65) Prior Publication Data

US 2015/0111210 A1 Apr. 23, 2015

Related U.S. Application Data

(63) Continuation of application No. 14/380,666, filed as application No. PCT/US2013/027457 on Feb. 22, 2013.

(60) Provisional application No. 61/603,091, filed on Feb. 24, 2012, provisional application No. 61/725,401, filed on Dec. 11, 2012.

(51) Int. Cl.
  *C12Q 1/68* (2018.01)
  *C12Q 1/689* (2018.01)

(52) U.S. Cl.
  CPC ....... *C12Q 1/689* (2013.01); *C12Q 2600/158* (2013.01); *C12Q 2600/16* (2013.01)

(58) Field of Classification Search
  CPC .................................................... C12Q 1/689
  See application file for complete search history.

(56) References Cited

U.S. PATENT DOCUMENTS

| 2003/0050470 | A1* | 3/2003 | An ........................ | C07H 21/00 536/24.3 |
| 2003/0215814 | A1* | 11/2003 | Cockerill, III ......... | C12Q 1/689 435/5 |
| 2006/0051769 | A1 | 3/2006 | Barts | |
| 2009/0226469 | A1 | 9/2009 | Smith et al. | |
| 2015/0031557 | A1 | 1/2015 | Tyler | |
| 2015/0111210 | A1 | 4/2015 | Tyler | |

FOREIGN PATENT DOCUMENTS

| CN | 101082581 A | 12/2007 |
| EP | 1380655 A2 | 1/2004 |

OTHER PUBLICATIONS

Auvray F, Lecureuil C, Dilasser F, Taché J, Derzelle S. Development of a real-time PCR assay with an internal amplification control for the screening of Shiga toxin-producing *Escherichia coli* in foods. Lett Appl Microbiol. May 2009; 48(5):554-9. Epub Feb. 9, 2009.*

Lee JE, Reed J, Shields MS, Spiegel KM, Farrell LD, Sheridan PP. Phylogenetic analysis of Shiga toxin 1 and Shiga toxin 2 genes associated with disease outbreaks. BMC Microbiol. Dec. 4, 2007; 7:109 pp. 1-12.*
Lowe T, Sharefkin J, Yang SQ, Dieffenbach CW. A computer program for selection of oligonucleotide primers for polymerase chain reactions. Nucleic Acids Res.Apr. 11, 1990; 18(7):1757-61.*
SantaLucia Jr, John. Physical principles and visual-OMP software for optimal PCR design. PCR Primer Design. Humana Press, 2007: pp. 3-33.*
Genbank Accession No. EF441617—*Escherichia coli* strain I8257 Shiga toxin 2 A subunit and Shiga toxin 2 B subunit genes, complete cds (submitted by Lee et al. Feb. 15, 2007, retrieved on Sep. 14, 2017 from http://www.ncbi.nlm.nih.gov/nuccore/EF441617).*
Genbank Accession No. AF461169—*Escherichia coli* EK921 Shiga toxin 1A subunit (stx1A) and Shiga toxin 1B subunit (stx1B) genes, complete cds (submitted by Yu et al. Dec. 19, 2001, retrieved on Sep. 14, 2017 from http://www.ncbi.nlm.nih.gov/nuccore/AF461169).*
Hoorfar J, Cook N, Malorny B, Wagner M, De Medici D, Abdulmawjood A, Fach P. Making internal amplification control mandatory for diagnostic PCR. J Clin Microbiol. Dec. 2003; 41(12):5835.*
Hoorfar J, Cook N, Malorny B, Wagner M, De Medici D, Abdulmawjood A, Fach P. Diagnostic PCR: making internal amplification control mandatory. Lett Appl Microbiol. 2004; 38(2):79-80.*
Genbank Accession No. AF175707—*Escherichia coli* verocytotoxin subunit A (vta) and verocytotoxin subunit B (vtb) genes, complete cds (submitted Aug. 4, 1999, retrieved on Jan. 29, 2020 from http://www.ncbi.nlm.nih.gov/nuccore/AF175707). (Year: 1999).*
Genbank Accession No. M23980—Bacteriophage H30 shiga-like toxin (SLT) gene encoding the A and B subunits, complete cds. (submitted Apr. 28, 1993, retrieved on Jan. 29, 2020 from http://www.ncbi.nlm.nih.gov/nuccore/M23980). (Year: 1993).*
Perelle S, Dilasser F, Grout J, Fach P. Detection by 5'-nuclease PCR of Shiga-toxin producing *Escherichia coli* O26, O55, O91, O103, O111, O113, O145 and O157:H7, associated with the world's most frequent clinical cases. Mol Cell Probes. Jun. 2004; 18(3): 185-92. (Year: 2004).*
EPO, Communication Pursuant to to Article 94(3) EPC, European Application No. 13708590.8, dated Mar. 4, 2016.
Chui et al., "Comparison of Shiga Toxin-Producing *Escherichia coli* Detection Methods Using Clinical Stool Samples," J Mol Diagn., 2010, 12(4):469-475, American Society for Investigative Pathology and the Association for Molecular Pathology, USA.
Basselet, et al. "Sample Processing for DNA Chip Array-Based Analysis of Enterohemorrhagic *Escherichia coli* (EHEC)," Microb Cell Fact, 2008, 7(1):1-10, London: BioMed Central.
Hidaka et al., "Multiplex Real-Time PCR for Exhaustive Detection of Diarrhoeagenic *Escherichia coli*," J Appl Micobiol., 2009, 106(2):410-420, Oxford: Published for the Society for Applied Bacteriology by Blackwell Science.

(Continued)

*Primary Examiner* — Teresa E Strzelecka
*Assistant Examiner* — Olayinka A Oyeyemi
(74) *Attorney, Agent, or Firm* — Jeffrey E. Landes; Adam M. Breier; Kristin J. McNamara

(57) ABSTRACT

The disclosed invention is related to methods, compositions and kits for targeting nucleic acid derived from Shiga toxin-producing bacteria such as *E. coli*. Compositions include amplification oligomers and/or detection probe oligomers. Kits and methods comprise at least one pair of amplification oligomers.

50 Claims, No Drawings

Specification includes a Sequence Listing.

(56) References Cited

OTHER PUBLICATIONS

Yu et al., "*Escherichia coli* EK921 Shiga Toxin 1A Subunit (stx1A) and Shia Toxin 1B Subunit (stx1B) Genes, Complete cds," GenBank, 2002, AF461169.1, National Center for Biotechnology Information.
Lee et al., "*Escherichia coli* Strain I8257 Shiga Toxin 2 A Subunit and Shiga Toxin 2 B Subunit Genes, Complete cds," GenBank, 2007, EF441617.1, National Center for Biotechnology Information.
International Search Report, International Application No. PCT/US2013/027457, dated Aug. 26, 2013.
Written Opinion of the International Searching Authority, International Application No. PCT/US2013/027457, dated Aug. 26, 2013.
International Preliminary Report on Patentability, International Application No. PCT/US2013/027457, dated Aug. 26, 2014.
Basselet et al., "Sample processing for DNA chip array-based analysis of enterohemorrhagic *Escherichia coli* (EHEC)", Microbial Cell Factories, Oct. 13, 2008 (Oct. 13, 2008). p. 29, vol. 7, No. 1, BioMed Central, London.
Chui et al. "Comparison of Shiga Toxin-Producing *Escherichia coli* Detection Methods Using Clinical Stool Samples", The Journal of Molecular Diagnostics, Jul. 1, 2010 (Jul. 1, 2010), pp. 469-475, vol. 12. No. 4, American Society for Investigative Pathology and the Association for Molecular Pathology.
Database GenBank [Online], Jul. 1, 2002 (Jul. 1, 2002), anonymous: "*Escherichia coli* EK921 Shiga toxin 1A subunit (stx1A) and Shiga toxin 1B subunit (stx1B) genes. complete cds", XP002698639, retrieved from NCBI, Database accession No. AF461169.1.
Database GenBank [Online], Dec. 21, 2007 (Dec. 21, 2007), anonymous: "*Escherichia coli* strain I8257 Shiga toxin 2 A subunit and Shiga toxin 2 B subunit genes, complete cds", XP002698640, retrieved from NCBI, Database accession No. EF441617.1.
Hidaka et al., "Multiplex real-time PCR for exhaustive detection of diarrhoeagenic *Escherichia coli*", Journal of Applied Microbiology, Feb. 1, 2009 (Feb. 1, 2009), pp. 410-420, vol. 106, No. 2, The Authors, The Society for Applied Microbiology.
Patent Examination Report, Australia Patent Application No. 2013205010, dated Jan. 2, 2015.
APO Examination Report No. 1, Australian Patent Application No. 2016231663, dated Oct. 16, 2017.
Perelle et al., "Detection by 5'-nuclease PCR of Shiga-toxin producing *Escherichia coli* O26, O55, O91, O103, O111, O113, O145 and O157:H7, associated with the world's most frequent clinical cases," Molecular and Cellular Probes, 2004, vol. 18, pp. 185-192.
CIPO Examination Report, Canadian Application No. 2,865,281, dated Nov. 30, 2018.
EPO Partial European Search Report, European Application No. 18201363.1, dated Dec. 21, 2018.
EPO Invitation pursuant to Article 94(3) and Rule 71(1) EPC, European Application No. 13708590.8, Nov. 9, 2017.
EPO Decision to Grant, European Application No. 13708590.8, dated Oct. 5, 2018.
APO Patent Examination Report No. 3, Australian Patent Application No. 2013205010, dated Aug. 26, 2016.
APO Patent Examination Report No. 2, Australian Patent Application No. 2013205010, dated Jun. 3, 2016.
APO Notice of Acceptance, Australian Patent Application No. 2013205010, dated Oct. 5, 2016.
APO Examination Report No. 1, Australian Patent Application No. 2016203539, dated Feb. 23, 2017.
APO Notice of Acceptance, Australian Patent Application No. 2016231663, dated Oct. 23, 2018.
APO Patent Examination Report No. 2, Australian Patent Application No. 2016231663, dated Jun. 13, 2018.
APO Notice of Grant, Australian Patent Application No. 2016253588, dated Jan. 10, 2019.
APO Examination Report No. 2, Australian Application No. 2016231663, dated Jun. 13, 2018.
APO Examination Report No. 2, Australian Application No. 2016253588, dated Jun. 14, 2018.
Blast Analysis of Cockerill SEQ ID No. 1 (May 2, 2018), generated in U.S. Appl. No. 14/380,666.
Blast Analysis of Cockerill SEQ ID No. 2 (May 2, 2018), generated in U.S. Appl. No. 14/380,666.
Blast Analysis of instant SEQ ID No. 30 (May 2, 2018), generated in U.S. Appl. No. 14/380,666.
Blast Analysis of instant SEQ ID No. 31 (May 2, 2018), generated in U.S. Appl. No. 14/380,666.
Blast Analysis of instant SEQ ID No. 32 (May 2, 2018), generated in U.S. Appl. No. 14/380,666.
Declaration under 37 C.F.R. § 1.132 of Paul Darby, filed in U.S. Appl. No. 14/380,666 on Sep. 19, 2018, 10 pages.
Henriques et al. "In silica vs in vitro analysis of primer specificity for the detection of Gardnerella vagina/is, Atopobium vaginae and *Lactobacillus* spp." BMC Research Notes 5: 637, pp. 1-4 (2012).
Office Action issued in European Application No. 13708590.8 dated Mar. 4, 2016.
Office Action issued in European Application No. 13708590.8 dated Sep. 11, 2017.
Response to Office Action in European Application No. 13708590.8 dated May 12, 2017, J. Lloyd.
Sambrook et al. Molecular cloning: A Laboratory Manual. Ed. 4, vol. 2. Cold Spring harbor laboratory press, (2012) 54 pages.
Smith and Osborn "Advantages and limitation of quantitative PCR (Q-PCR)-based approaches in microbial ecology," FEMS Microbiol Ecol. 67(1): 6-20 (2009).
Bai et al. "Enhancement of PCR Sensitivity and Yield Using Thiol-modified Primers," *Scientific Reports* 8: 14858 (2008) (8 pages).
Kalvatchev et al. "Effective Light-Upon-Extension Real-Time PCR Primer Systems for Rapid Detection of Human Viruses," *Labmedicine*, 41(3): 150-155 (2010).
Kurata et al. "Fluorescent quenching-based quantitative detection of specific DNA/RNA using a BODIPY® FL-labeled probe or primer," *Nucleic Acids Research*, 29(6): e34 (2001) (5 pages).
Lebedev et al. "Hot Start PCR with heat-activatable primers: a novel approach for improved PCT performance," *Nucleic Acids Research*, 36(20): e131. (2008).
Lebedev et al. "Oligonucleotides containing 2-aminoadenine and 5-methylcytosine are more effective as primers for PCR amplification than their nonmodified counterparts," *Genetic Analysis: Biomolecular Engineering*, 13: 15-21 (1996).
Nazarenko et al. "Multiplex quantitative PCR using self-quenched primers labeled with a single fluorophore," *Nucleic Acids Research*, 30(9): e37 (2002) (7 pages).
Schneider et al. "Improved Efficiency and Robustness in qPCR and Multiplex End-Point PCR by Twisted Intercalating Nucleic Acid Modified Primers," *PLoS One*, 7(6): e38451 (2012) (11 pages).
Schoenbrunner et al. "Covalent modification of primers improves PCR amplification specificity and yield," *Biology Methods and Protocols*, 2017: 1-10 (2017).
Shum and Paul "Chemically modified primers for improved multiplex polymerase chain reaction," *Analytical Biochemistry*, 388: 266-272 (2009).
EPO Examination Report, European Application No. 18201363.1, dated Mar. 12, 2020, 6 pages.
Response to Examination Report, European Application No. 18201363.1, dated Oct. 24, 2019, 12 pages.
EPO Extended Search Report, European Application No. 18201363.1, dated Apr. 3, 2019, 13 pages.

\* cited by examiner

DETECTION OF SHIGA TOXIN GENES IN BACTERIA

CROSS-REFERENCE TO RELATED APPLICATIONS

This present application is a non-provisional application and claims the benefit of 61/603,091, filed Feb. 24, 2012, and 61/725,401, filed Nov. 12, 2012, both of which are incorporated by reference in their entireties for all purposes.

FIELD OF THE INVENTION

The present invention relates to the detection of infectious agents, more specifically to the detection of Shiga toxin genes. Compositions, methods and kits are described for the detection of Shiga toxin genes by using in vitro nucleic acid amplification techniques.

BACKGROUND OF THE INVENTION

*Escherichia coli* (*E. coli*) is a gram-negative, rod-shaped bacterium that is commonly found in the lower intestine of warm-blooded organisms. Most strains of *E. coli* are non-pathogenic and are part of the normal gut flora. However, some serotypes can cause life-threatening infections in humans. Pathogenic strains of *E. coli* can cause gastroenteritis, urinary tract infections, neonatal meningitis, haemolytic-uremic syndrome, peritonitis, mastitis, septicemia and pneumonia.

*E. coli* has the ability to transfer DNA to and from other bacteria. This ability has allowed some strains of *E. coli* to acquire the bacteriophage carrying the genes encoding Shiga toxin from *Shigella*. There are two main types of Shiga toxin produced by certain strains of *E. coli*, Shiga toxin type 1 and Shiga toxin type 2, which are carried on two different genes, stx1 and stx2, respectively. Some strains of *E. coli* contain the stx1 gene while other strains contain the stx2 gene. There are also certain strains of *E. coli* that contain both the stx1 and stx2 genes. The most common strain of Shiga toxin-producing *E. coli* (STEC) in North America is O157:H7, however, there are over one hundred strains of *E. coli* that can produce Shiga toxin. In addition to *E. coli*, *Citrobacter freundii*, *Aeromononas hydrophile*, *Aeromononas caviae*, and *Enterobacter cloacae* have also been reported to be able to produce Shiga toxin.

Shiga toxins bind to specific cell surfaces via glycolipid Gb3. Once bound to the cell, Shiga toxins enter the cell and shut down protein synthesis, which leads to cell death. In STEC, the Shiga toxin binds to the vascular endothelium of small blood vessels. The killing of vascular endothelium cells leads to the breakdown of the lining of the small blood vessels, which in turn results in haemorrhaging. Because STEC infections usually occur from ingesting contaminated food or water, the first symptom is generally bloody diarrhea. As the infection progresses, the toxin can spread to the kidneys, causing haemolytic uremic syndrome which affects the lungs, and nervous system. STEC infections occur in the United States at a rate of about 0.9 individuals per 100,000 for *E. coli* O157 and at a rate of about 1 individual per 100,000 for strains other than O157.

Routine methods for detecting Shiga toxin producing *E. coli* (STEC) involve analysis of stool cultures and/or enzyme immunoassays. Stool culture takes approximately 24 hours when grown on defined media. However, selective and differential media are only available for identifying O157:H7. Because of the lack of media available, most labs do not have the capabilities to test for non-O157 STEC serotypes. Labs are required to send non-O157 isolates to their local or state labs for more complex testing such as pulse-field gel electrophoresis typing and virulence gene characterization. This is beyond the capabilities of many labs. Enzyme immunoassays (EIAs) detect Shiga toxins via anti-Shiga toxin capture antibodies absorbed to micro-wells. Diluted samples are added to the wells and incubated, washed and then anti-Shiga toxin antibodies are added. This is followed by more incubation and washing. Enzyme conjugated anti-IgG polyclonal antibody is added and incubated and if a Shiga toxin is present, a reactive antibody-enzyme complex is formed and a substrate solution is added to elicit a colored response in samples containing the Shiga toxin. A stop solution is then added and the results are interpreted. The EIAs may be used directly on stool specimens. However, these procedures have been found to be more sensitive if the stool specimen is subject to overnight broth enrichment. These EIAs can detect O157 and non-O157 STEC strains but with the need to incubate stool specimens overnight to maximize sensitivity, the tests take too long to generate answers. Thus, there is a need for an assay for the detection of STEC from a number of *E. coli* strains. There is a need in the art for an assay that rapidly detects STEC. There also is a need for an assay that specifically detects STEC. Additionally, there is a need for an assay that detects STEC with a high degree of sensitivity.

SUMMARY OF THE INVENTION

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

The present invention relates to methods, compositions, kits and amplification products for identification of stx1 and stx2 genes.

One aspect of the invention relates to a method for identifying a stx1 gene in a sample. The method includes the step of contacting the sample with a pair of amplification oligomers. Each member of the pair of amplification oligomers has a length of from about 15 to about 25 contiguous nucleotides. The pair of amplification oligomers typically includes an oligomer pair selected from the group consisting of (i) a first oligomer having at least 90%, at least 95%, or 100% sequence identity to SEQ ID NO:30 and a second oligomer having at least 90%, at least 95%, or 100% sequence identity to SEQ ID NO:31; (ii) a first oligomer having at least 90%, at least 95%, or 100% sequence identity to SEQ ID NO:1 and a second oligomer having at least 90%, at least 95%, or 100% sequence identity to SEQ ID NO:2; (iii) a first oligomer having at least 90%, at least 95%, or 100% sequence identity to SEQ ID NO:8 and a second oligomer having at least 90%, at least 95%, or 100% sequence identity to SEQ ID NO:9; (iv) a first oligomer having at least 90%, at least 95%, or 100% sequence identify to SEQ ID NO:12 and a second oligomer having at least 90%, at least 95%, or 100% sequence identity to SEQ ID NO:13; and (v) a first oligomer having at least 90%, at least 95%, or 100% sequence identity to SEQ ID NO:19 and a second oligomer having at least 90%, at least 95%, or 100% sequence identity to SEQ ID NO:20. The method includes the step of amplifying nucleic acid in the sample with the pair of amplification oligomers to obtain an amplification product. The method also includes the step of determining the sequence of the amplification product or detecting the amplification product using a detection probe.

In certain embodiments of the method for identifying a stx1 gene, the sample may contain bacterial nucleic acid originating from *Escherichia coli, Citrobacter freundii, Aeromononas hydrophile, Aeromononas caviae*, or *Enterobacter cloacae*. In certain embodiments of the method for identifying a stx1 gene, the bacterial nucleic acid originates from a strain of *E. coli* such as *E. coli* O157:H7.

In certain embodiments of the method for identifying a stx1 gene, the amplification step is performed using the polymerase chain reaction. In certain embodiments, the polymerase chain reaction is a real-time polymerase chain reaction.

In certain embodiments of the method for identifying a stx1 gene, the detection probe is a capture probe or a fluorescence probe. The fluorescence probe can include a fluorescent dye compound and a non-fluorescent quenching dye compound.

In certain embodiments of the method for identifying a stx1 gene, the probe is an oligomer having a length of from about 15 to about 30, to about 35, or to about 40 contiguous oligomer residues. In certain embodiments of the method for identifying a stx1 gene, (i) for an amplification oligomer pair corresponding to SEQ ID NOS:30 and 31, the probe has at least 90%, at least 95% or 100% sequence identity to SEQ ID NO:32; (ii) for an amplification oligomer pair corresponding to SEQ ID NOS:1 and 2, the probe has at least 90%, at least 95%, or 100% sequence identity to SEQ ID NO:5; (iii) for an amplification oligomer pair corresponding to SEQ ID NOS:8 and 9, the probe has at least 90%, at least 95%, or 100% sequence identity to SEQ ID NO:11; (iv) for an amplification oligomer pair corresponding to SEQ ID NOS:12 and 13, the probe has at least 90%, at least 95%, or 100% sequence identity to SEQ ID NO:14; or (v) for an amplification oligomer pair corresponding to SEQ ID NOS: 19 and 20, the probe has at least 90%, at least 95%, or 100% sequence identity to SEQ ID NO:22.

In certain embodiments of the method for identifying a stx1 gene, the step of determining the sequence of the amplification product is performed by a sequencing reaction, a microarray, electrophoresis, or mass spectrometry.

Another aspect of the invention relates to a primer pair for amplification of a stx1 gene. The primer pair includes a pair of amplification oligomers with each member of the pair typically having a length of from about 15 to about 25 contiguous nucleotides. In particular embodiments, the pair of amplification oligomers includes an oligomer pair selected from the group consisting of (i) a first oligomer having at least 90%, at least 95%, or 100% sequence identity to SEQ ID NO:30 and a second oligomer having at least 90%, at least 95%, or 100% sequence identity to SEQ ID NO:31; (ii) a first oligomer having at least 90%, at least 95%, or 100% sequence identity to SEQ ID NO:1 and a second oligomer having at least 90%, at least 95%, or 100% sequence identity to SEQ ID NO:2; (iii) a first oligomer having at least 90%, at least 95%, or 100% sequence identity to SEQ ID NO:8 and a second oligomer having at least 90%, at least 95%, or 100% sequence identity to SEQ ID NO:9; (iv) a first oligomer having at least 90%, at least 95%, or 100% sequence identify to SEQ ID NO:12 and a second oligomer having at least 90%, at least 95%, or 100% sequence identity to SEQ ID NO:13; and (v) a first oligomer having at least 90%, at least 95%, or 100% sequence identity to SEQ ID NO:19 and a second oligomer having at least 90%, at least 95%, or 100% sequence identity to SEQ ID NO:20.

Another aspect of the invention relates to a primer-probe set for detection of a stx1 gene. The primer-probe set includes a pair of amplification oligomers with each member of the pair typically having a length of from about 15 to about 25 contiguous nucleotides. In particular embodiments, the primer probe set includes (1) a pair of amplification oligomers selected from the group consisting of (i) a first oligomer having at least 90%, at least 95%, or 100% sequence identity to SEQ ID NO:30 and a second oligomer having at least 90%, at least 95%, or 100% sequence identity to SEQ ID NO:31; (ii) a first oligomer having at least 90%, at least 95%, or 100% sequence identity to SEQ ID NO:1 and a second oligomer having at least 90%, at least 95%, or 100% sequence identity to SEQ ID NO:2; (iii) a first oligomer having at least 90%, at least 95%, or 100% sequence identity to SEQ ID NO:8 and a second oligomer having at least 90%, at least 95%, or 100% sequence identity to SEQ ID NO:9; (iv) a first oligomer having at least 90%, at least 95%, or 100% sequence identify to SEQ ID NO:12 and a second oligomer having at least 90%, at least 95%, or 100% sequence identity to SEQ ID NO:13; and (v) a first oligomer having at least 90%, at least 95%, or 100% sequence identity to SEQ ID NO:19 and a second oligomer having at least 90%, at least 95%, or 100% sequence identity to SEQ ID NO:20; and (2) an oligomer probe which is hybridizable to a stx1 gene region located between the regions of hybridization of the pair of amplification oligomers. In certain embodiments, the probe has a length of from about 10 to about 30, to about 35, or to about 40 contiguous oligomer residues. In certain embodiments, (i) for an amplification oligomer pair corresponding to SEQ ID NOS:30 and 31, the probe has at least 90%, at least 95% or 100% sequence identity to SEQ ID NO:32; (ii) for an amplification oligomer pair corresponding to SEQ ID NOS:1 and 2, the probe has at least 90%, at least 95%, or 100% sequence identity to SEQ ID NO:5; (iii) for an amplification oligomer pair corresponding to SEQ ID NOS:8 and 9, the probe has at least 90%, at least 95%, or 100% sequence identity to SEQ ID NO:11; (iv) for an amplification oligomer pair corresponding to SEQ ID NOS:12 and 13, the probe has at least 90%, at least 95%, or 100% sequence identity to SEQ ID NO:14; or (v) for an amplification oligomer pair corresponding to SEQ ID NOS:19 and 20, the probe has at least 90%, at least 95%, or 100% sequence identity to SEQ ID NO:22. In certain embodiments, the primer-probe set further includes an internal control system for verifying reaction conditions. The system includes a control template polynucleotide, a pair of control amplification oligomers and a control probe.

Another aspect of the invention relates to a method for identifying a stx2 gene in a sample. The method includes the step of contacting the sample with a pair of amplification oligomers. Each member of the pair of amplification oligomers has a length of from about 15 to about 25 contiguous nucleotides. The pair of amplification oligomers typically includes an oligomer pair selected from the group consisting of (i) a first oligomer having at least 90%, at least 95%, or 100% sequence identity to SEQ ID NO:33 and a second oligomer having at least 90%, a least 95%, or 100% sequence identity to SEQ ID NO:34; (ii) a first oligomer having at least 90%, at least 95%, or 100% sequence identity to SEQ ID NO:40 and a second oligomer having at least 90%, at least 95%, or 100% sequence identity to SEQ ID NO:41; (iii) a first oligomer having at least 90%, at least 95%, or 100% sequence identity to SEQ ID NO:36 and a second oligomer having at least 90%, at least 95%, or 100% sequence identity to SEQ ID NO:37; and (iv) a first oligomer having at least 90%, at least 95%, or 100% sequence identity to SEQ ID NO:47 and a second oligomer having at least 90%, at least 95%, or 100% sequence identity to SEQ ID NO:48. The method includes the step of amplifying nucleic acid in the sample with the pair of amplification oligomers to obtain an amplification product. The method also includes the step of determining the sequence of the amplification product or detecting the amplification product using a detection probe.

In certain embodiments of the method for identifying a stx2 gene, the sample may contain bacterial nucleic acid originating from *E. coli, Citrobacter freundii, Aeromononas hydrophile, Aeromononas caviae*, or *Enterobacter cloacae*. In certain embodiments of the method for identifying a stx2 gene, the nucleic acid originates from a strain of *Escherichia coli* such as *E. coli* 0157:H7.

In certain embodiments of the method for identifying a stx2 gene, the amplification step is performed using the polymerase chain reaction. In certain embodiments, the polymerase chain reaction is a real-time polymerase chain reaction.

In certain embodiments of the method for identifying a stx2 gene, the detection probe is a capture probe or a fluorescence probe. The fluorescence probe can include a fluorescent dye compound and a non-fluorescent quenching dye compound.

In certain embodiments of the method for identifying a stx2 gene, the probe is an oligomer having a length of from about 15 to about 30, to about 35, or to about 40 contiguous oligomer residues. In certain embodiments of the method for identifying a stx2 gene, for the amplification oligomer pair of (i), the probe has at least 90%, at least 95%, or 100% sequence identity to SEQ ID NO:35; for the amplification oligomer pair of (ii), the probe has at least 90%, at least 95%, or 100% sequence identity to SEQ ID NO:42; for the amplification oligomer pair of (iii), the probe has at least 90%, at least 95%, or 100% sequence identity to SEQ ID NO:39, or (iv) for the amplification oligomer pair of (iv), the probe has at least 90%, at least 95%, or 100% sequence identity to SEQ ID NO:49.

In certain embodiments of the method for identifying a stx2 gene, the step of determining the sequence of the amplification product is performed by a sequencing reaction, a microarray, electrophoresis, or mass spectrometry.

Another aspect of the invention relates to a primer pair for amplification of a stx2 gene. The primer pair includes a pair of amplification oligomers with each member of the pair having a length of from about 15 to about 25 contiguous nucleotides. The pair of amplification oligomers includes an oligomer pair selected from the group consisting of (i) a first oligomer having at least 90%, at least 95%, or 100% sequence identity to SEQ ID NO:33 and a second oligomer having at least 90%, a least 95%, or 100% sequence identity to SEQ ID NO:34; (ii) a first oligomer having at least 90%, at least 95%, or 100% sequence identity to SEQ ID NO:40 and a second oligomer having at least 90%, at least 95%, or 100% sequence identity to SEQ ID NO:41; (iii) a first oligomer having at least 90%, at least 95%, or 100% sequence identity to SEQ ID NO:36 and a second oligomer having at least 90%, at least 95%, or 100% sequence identity to SEQ ID NO:37; and (iv) a first oligomer having at least 90%, at least 95%, or 100% sequence identity to SEQ ID NO:47 and a second oligomer having at least 90%, at least 95%, or 100% sequence identity to SEQ ID NO:48.

Another aspect of the invention relates to a primer-probe set for detection of a stx2 gene. The primer probe set includes a pair of amplification oligomers with each member of the pair typically having a length of from about 15 to about 25 contiguous nucleotides. In particular embodiments, the primer-probe set includes (1) a pair of amplification oligomers selected from the group consisting of (i) a first oligomer having at least 90%, at least 95%, or 100% sequence identity to SEQ ID NO:33 and a second oligomer having at least 90%, a least 95%, or 100% sequence identity to SEQ ID NO:34; (ii) a first oligomer having at least 90%, at least 95%, or 100% sequence identity to SEQ ID NO:40 and a second oligomer having at least 90%, at least 95%, or 100% sequence identity to SEQ ID NO:41; (iii) a first oligomer having at least 90%, at least 95%, or 100% sequence identity to SEQ ID NO:36 and a second oligomer having at least 90%, at least 95%, or 100% sequence identity to SEQ ID NO:37; and (iv) a first oligomer having at least 90%, at least 95%, or 100% sequence identity to SEQ ID NO:47 and a second oligomer having at least 90%, at least 95%, or 100% sequence identity to SEQ ID NO:48; and (2) an oligomer probe which is hybridizable to a stx2 gene region located between the regions of hybridization of the pair of amplification oligomers. In certain embodiments, the probe has a length of from about 10 to about 30, to about 35, or to about 40 contiguous oligomer residues. In certain embodiments, for the amplification oligomer pair of (i), the probe has at least 90%, at least 95%, or 100% sequence identity to SEQ ID NO:35; for the amplification oligomer pair of (ii), the probe has at least 90%, at least 95%, or 100% sequence identity to SEQ ID NO:42; for the amplification oligomer pair of (iii), the probe has at least 90%, at least 95%, or 100% sequence identity to SEQ ID NO:39, or (iv) for the amplification oligomer pair of (iv), the probe has at least 90%, at least 95%, or 100% sequence identity to SEQ ID NO:49. In certain embodiments, the primer-probe set further includes an internal control system for verifying reaction conditions. The system includes a control template polynucleotide, a pair of control amplification oligomers and a control probe.

Another aspect of the invention relates to a kit for amplification of a stx1 gene. The kit includes the primer pair for amplification of a stx1 gene as described above, optionally in combination with instructions for carrying out a polymerase chain reaction using the amplification oligomers.

Another aspect of the invention relates to a kit for detection of a stx1 gene. The kit includes at least one of the embodiments of the primer-probe sets for amplification of a stx1 gene as described above, optionally in combination with instructions for carrying out a polymerase chain reaction using the amplification oligomers.

Another aspect of the invention relates to a kit for amplification of a stx2 gene. The kit includes at the primer pair for amplification of a stx2 gene as described above, optionally in combination with instructions for carrying out a polymerase chain reaction using the amplification oligomers.

Another aspect of the invention relates to a kit for detection of a stx2 gene. The kit includes at least one of the embodiments of the primer-probe sets for amplification of a stx2 gene as described above, optionally in combination with instructions for carrying out a polymerase chain reaction using the amplification oligomers.

Another aspect of the invention relates to a kit for amplification of a stx1 gene and a stx2 gene. The kit includes the primer pair for amplification of a stx1 gene described above, and the primer pair for amplification of a stx2 gene described above.

Another aspect of the invention relates to a kit for detection of a stx1 gene and a stx2 gene. The kit includes any of the embodiments of the primer-probe sets for identification of stx1 as described above, in combination with any of the embodiments of the primer-probe sets for identification of stx2 as described above.

Another aspect of the invention relates to an amplification product for identification of a stx1 gene. This amplification product is produced by any of the embodiments of the method for identifying a stx1 gene as described above.

Another aspect of the invention relates to an amplification product for identification of a stx2 gene. This amplification product is produced by any of the embodiments of the method for identifying a stx2 gene as described above.

In another aspect, the present invention provides a method for identifying at least one of a stx1 gene and a stx2 gene in a sample. The method generally includes contacting the sample with a pair of stx1-specific amplification oligomers and a pair of stx2-specific amplification oligomers. Typically, each member of said stx1-specific and stx2-specific pairs of amplification oligomers has a length of from about 15 to about 25 contiguous nucleotides. In particular embodiments, the pair of stx1-specific amplification oligomers includes an oligomer pair selected from the following: (1-i) a first oligomer having at least 90%, at least 95% or 100% sequence identity to SEQ ID NO:30 and a second oligomer having at least 90%, at least 95%, or 100% sequence identity to SEQ ID NO:31; (1-ii) a first oligomer having at least 90%, at least 95%, or 100% sequence identity to SEQ ID NO:1 and a second oligomer having at least 90%, at least 95%, or 100% sequence identity to SEQ ID NO:2; (1-iii) a first oligomer having at least 90%, at least 95%, or 100% sequence identity to SEQ ID NO: 8 and a second oligomer having at least 90%, at least 95%, or 100% sequence identity to SEQ ID NO: 9; (1-iv) a first oligomer having at least 90%, at least 95%, or 100% sequence identify to SEQ ID NO:12 and a second oligomer having at least 90%, at least 95%, or 100% sequence identity to SEQ ID NO:13; and (1-v) a first oligomer having at least 90%, at least 95%, or 100% sequence identity to SEQ ID NO:19 and a second oligomer having at least 90%, at least 95%, or 100% sequence identity to SEQ ID NO:20. In particular embodiments, the pair of stx2-specific amplification oligomers includes an oligomer pair selected from the following: (2-i) a first oligomer having at least 90%, at least 95%, or 100% sequence identity to SEQ ID NO:33 and a second oligomer having at least 90%, at least 95%, or 100% sequence identity to SEQ ID NO:34; (2-ii) a first oligomer having at least 90%, at least 95%, or 100% sequence identity to SEQ ID NO:40 and a second oligomer having at least 90%, at least 95%, or 100% sequence identity to SEQ ID NO:41; (2-iii) a first oligomer having at least 90%, at least 95%, or 100% sequence identity to SEQ ID NO: 36 and a second oligomer having at least 90%, at least 95%, or 100% sequence identity to SEQ ID NO: 37; and (2-iv) a first oligomer having at least 90%, at least 95%, or 100% sequence identity to SEQ ID NO:47 and a second oligomer having at least 90%, at least 95%, or 100% sequence identity to SEQ ID NO:48. The method further includes amplifying nucleic acid in the sample with the stx1-specific and/or stx2-specific pairs of amplification oligomers to obtain at least one amplification product, and determining the sequence of the at least one amplification product or detecting the at least one amplification product using a stx1-specific detection probe and a stx2-specific detection probe.

In some variations of a method as above for identifying at least one of stx1 and stx2 in a sample, each of the stx1-specific and stx2-specific detection probes is an oligomer having a length of from about 15 to about 30 contiguous oligomer residues. In particular embodiments, for the amplification oligomer pair of (1-i), the stx1-specific probe has at least 90%, at least 95%, or 100% sequence identity to SEQ ID NO:32; for the amplification oligomer pair of (1-ii), the stx1-specific probe has at least 90%, at least 95%, or 100% sequence identity to SEQ ID NO:5; for the amplification oligomer pair of (1-iii), the stx1-specific probe has at least 90%, at least 95%, or 100% sequence identity to SEQ ID NO: 11; for the amplification oligomer pair of (1-iv), the stx1-specific probe has at least 90%, at least 95%, or 100% sequence identity to SEQ ID NO:14; or for the amplification oligomer pair of (1-v), the stx1-specific probe has at least 90%, at least 95%, or 100% sequence identity to SEQ ID NO:22. In particular embodiments, for the amplification oligomer pair of (2-i), the stx2-specific probe has at least 90%, at least 95%, or 100% sequence identity to SEQ ID NO:35; for the amplification oligomer pair of (2-ii), the stx2-specific probe has at least 90%, at least 95%, or 100% sequence identity to SEQ ID NO:42; for the amplification oligomer pair of (2-iii), the stx2-specific probe has at least 90%, at least 95%, or 100% sequence identity to SEQ ID NO: 39; or for the amplification oligomer pair of (2-iv), the stx2-specific probe has at least 90%, at least 95%, or 100% sequence identity to SEQ ID NO:49.

In particular embodiments of a method as above for identifying at least one of stx1 and stx2 in a sample, the stx1-specific and stx2-specific pairs of amplification oligomers are selected from the following combinations of stx1-specific and stx2-specific oligomer pairs: (A) the amplification oligomer pairs of (1-i) and (2-i); (B) the amplification oligomer pairs of (1-i) and (2-ii); (C) the amplification oligomer pairs of (1-ii) and (2-i); (D) the amplification oligomer pairs of (1-iv) and (2-iv); (E) the amplification oligomer pairs of (1-v) and (2-i); and (F) the amplification oligomer pairs of (1-v) and (2-iv). In more specific variations of the method, for the combination of stx1-specific and stx2-specific oligomer pairs of (A), the stx1-specific probe has at least 90%, at least 95%, or 100% sequence identity to SEQ ID NO:32 and the stx2-specific probe has at least 90%, at least 95%, or 100% sequence identity to SEQ ID NO:35; for the combination of stx1-specific and stx2-specific oligomer pairs of (B), the stx1-specific probe has at least 90%, at least 95%, or 100% sequence identity to SEQ ID NO:32 and the stx2-specific probe has at least 90%, at least 95%, or 100% sequence identity to SEQ ID NO:42; for the combination of stx1-specific and stx2-specific oligomer pairs of (C), the stx1-specific probe has at least 90%, at least 95%, or 100% sequence identity to SEQ ID NO:5 and the stx2-specific probe has at least 90%, at least 95%, or 100% sequence identity to SEQ ID NO:35; for the combination of stx1-specific and stx2-specific oligomer pairs of (D), the stx1-specific probe has at least 90%, at least 95%, or 100% sequence identity to SEQ ID NO:14 and the stx2-specific probe has at least 90%, at least 95%, or 100% sequence identity to SEQ ID NO:49; for the combination of stx1-specific and stx2-specific oligomer pairs of (E), the stx1-specific probe has at least 90%, at least 95%, or 100% sequence identity to SEQ ID NO:22 and the stx2-specific probe has at least 90%, at least 95%, or 100% sequence identity to SEQ ID NO:35; or for the combination of stx1-specific and stx2-specific oligomer pairs of (F), the stx1-specific probe has at least 90%, at least 95%, or 100% sequence identity to SEQ ID NO:22 and the stx2-specific probe has at least 90%, at least 95%, or 100% sequence identity to SEQ ID NO:49.

In certain embodiments of a method as above for identifying at least one of stx1 and stx2 in a sample, the sample includes bacterial nucleic acid originating from *Escherichia coli, Citrobacter freundii, Aeromononas hydrophile, Aeromononas caviae*, or *Enterobacter cloacae*. In particular variations of the method, the bacterial nucleic acid originates from a strain of *E. coli* such as *E. coli* 0157:H7.

In some embodiments of the method for identifying at least one of stx1 and stx2 in a sample, the amplification step is performed using the polymerase chain reaction such as, for example, a real-time polymerase chain reaction.

In certain variations in which the detecting step includes detecting the at least one amplification product using the stx1-specific and stx2-specific detection probes, each of the detection probes is a fluorescence probe comprising a fluorescent dye compound. For example, each of the stx1-specific and stx2-specific detection probes may include a fluorescent dye compound and a non-fluorescent quenching dye compound.

In another aspect, the present invention provides a primer set for amplification of at least one of a stx1 gene and a stx2 gene in a sample. The primer set includes a pair of stx1-specific amplification oligomers and a pair of stx2-specific amplification oligomers, with each member of the pair typically having a length of from about 15 to about 25 contiguous nucleotides. In particular embodiments, the pair of stx1-specific amplification oligomers includes an oligomer pair selected from the following: (1-i) a first oligomer having at least 90%, at least 95%, or 100% sequence identity to SEQ ID NO:30 and a second oligomer having at least 90%, at least 95%, or 100% sequence identity to SEQ ID NO:31; (1-ii) a first oligomer having at least 90%, at least 95%, or 100% sequence identity to SEQ ID NO:1 and a second oligomer having at least 90%, at least 95%, or 100% sequence identity to SEQ ID NO:2; (1-iii) a first oligomer having at least 90%, at least 95%, or 100% sequence identity to SEQ ID NO: 8 and a second oligomer having at least 90%, at least 95%, or 100% sequence identity to SEQ ID NO: 9; (1-iv) a first oligomer having at least 90%, at least 95%, or 100% sequence identify to SEQ ID NO:12 and a second oligomer having at least 90%, at least 95%, or 100% sequence identity to SEQ ID NO:13; and (1-v) a first oligomer having at least 90%, at least 95%, or 100% sequence identity to SEQ ID NO:19 and a second oligomer having at least 90%, at least 95%, or 100% sequence identity to SEQ ID NO:20. In particular embodiments, the pair of stx2-specific amplification oligomers includes an oligomer pair selected from the following: (2-i) a first oligomer having at least 90%, at least 95%, or 100% sequence identity to SEQ ID NO:33 and a second oligomer having at least 90%, at least 95%, or 100% sequence identity to SEQ ID NO:34; (2-ii) a first oligomer having at least 90%, at least 95%, or 100% sequence identity to SEQ ID NO:40 and a second oligomer having at least 90%, at least 95%, or 100% sequence identity to SEQ ID NO:41; (2-iii) a first oligomer having at least 90%, at least 95%, or 100% sequence identity to SEQ ID NO: 36 and a second oligomer having at least 90%, at least 95%, or 100% sequence identity to SEQ ID NO: 37; and (2-iv) a first oligomer having at least 90%, at least 95%, or 100% sequence identity to SEQ ID NO:47 and a second oligomer having at least 90%, at least 95%, or 100% sequence identity to SEQ ID NO:48.

In particular embodiments of a primer set as above, the stx1-specific and stx2-specific pairs of amplification oligomers are selected from the following combinations of stx1-specific and stx2-specific oligomer pairs: (A) the amplification oligomer pairs of (1-i) and (2-i); (B) the amplification oligomer pairs of (1-i) and (2-ii); (C) the amplification oligomer pairs of (1-ii) and (2-i); (D) the amplification oligomer pairs of (1-iv) and (2-iv); (E) the amplification oligomer pairs of (1-v) and (2-i); and (F) the amplification oligomer pairs of (1-v) and (2-iv).

In another aspect, the present invention provides a kit for amplification of at least one of a stx1 gene and a stx2 gene, the kit comprising a primer set as set forth above.

In yet another aspect, the present invention provides a primer-probe set for identification of at least one of a stx1 gene and a stx2 gene in a sample. The primer-probe set includes a pair of stx1-specific amplification oligomers and a pair of stx2-specific amplification oligomers, with each member of the stx1-specific and stx2-specific pairs of amplification oligomers typically having a length of from about 15 to about 25 contiguous nucleotides. The primer-probe set further includes a stx1-specific detection probe hybridizable to a stx1 gene region located between the regions of hybridization of the pair of stx1-specific amplification oligomers, and a stx2-specific detection probe hybridizable to a stx2 gene region located between the regions of hybridization of the pair of stx2-specific amplification oligomers. In particular embodiments, the pair of stx1-specific amplification oligomers includes an oligomer pair selected from the following: (1-i) a first oligomer having at least 90%, at least 95%, or 100% sequence identity to SEQ ID NO:30 and a second oligomer having at least 90%, at least 95%, or 100% sequence identity to SEQ ID NO:31; (1-ii) a first oligomer having at least 90%, at least 95%, or 100% sequence identity to SEQ ID NO:1 and a second oligomer having at least 90%, at least 95%, or 100% sequence identity to SEQ ID NO:2; (1-iii) a first oligomer having at least 90%, at least 95%, or 100% sequence identity to SEQ ID NO: 8 and a second oligomer having at least 90%, at least 95%, or 100% sequence identity to SEQ ID NO: 9; (1-iv) a first oligomer having at least 90%, at least 95%, or 100% sequence identify to SEQ ID NO:12 and a second oligomer having at least 90%, at least 95%, or 100% sequence identity to SEQ ID NO:13; and (1-v) a first oligomer having at least 90%, at least 95%, or 100% sequence identity to SEQ ID NO:19 and a second oligomer having at least 90%, at least 95%, or 100% sequence identity to SEQ ID NO:20. In particular embodiments, the pair of stx2-specific amplification oligomers includes an oligomer pair selected from the following: (2-i) a first oligomer having at least 90%, at least 95%, or 100% sequence identity to SEQ ID NO:33 and a second oligomer having at least 90%, at least 95%, or 100% sequence identity to SEQ ID NO:34; (2-ii) a first oligomer having at least 90%, at least 95%, or 100% sequence identity to SEQ ID NO:40 and a second oligomer having at least 90%, at least 95%, or 100% sequence identity to SEQ ID NO:41; (2-iii) a first oligomer having at least 90%, at least 95%, or 100% sequence identity to SEQ ID NO: 36 and a second oligomer having at least 90%, at least 95%, or 100% sequence identity to SEQ ID NO: 37; and (2-iv) a first oligomer having at least 90%, at least 95%, or 100% sequence identity to SEQ ID NO:47 and a second oligomer having at least 90%, at least 95%, or 100% sequence identity to SEQ ID NO:48.

In certain variations of a primer-probe set as above each of the stx1-specific and stx2-specific detection probes is an oligomer having a length of from about 15 to about 30 or to about 40 contiguous oligomer residues. In particular embodiments, for the amplification oligomer pair of (1-i), the stx1-specific probe has at least 90%, at least 95%, or 100% sequence identity to SEQ ID NO:32; for the amplification oligomer pair of (1-ii), the stx1-specific probe has at least 90%, at least 95%, or 100% sequence identity to SEQ ID NO:5; for the amplification oligomer pair of (1-iii), the stx1-specific probe has at least 90%, at least 95%, or 100% sequence identity to SEQ ID NO: 11; for the amplification oligomer pair of (1-iv), the stx1-specific probe has at least 90%, at least 95%, or 100% sequence identity to SEQ ID NO:14; or for the amplification oligomer pair of (1-v), the stx1-specific probe has at least 90%, at least 95%, or 100% sequence identity to SEQ ID NO:22. In particular embodiments, for the amplification oligomer pair of (2-i), the stx2-specific probe has at least 90%, at least 95%, or 100% sequence identity to SEQ ID NO:35; for the amplification oligomer pair of (2-ii), the stx2-specific probe has at least 90%, at least 95%, or 100% sequence identity to SEQ ID NO:42; for the amplification oligomer pair of (2-iii), the stx2-specific probe has at least 90%, at least 95%, or 100% sequence identity to SEQ ID NO: 39; or for the amplification oligomer pair of (2-iv), the stx2-specific probe has at least 90%, at least 95%, or 100% sequence identity to SEQ ID NO:49.

In some variations of a primer-probe set as above, the stx1-specific and stx2-specific pairs of amplification oligomers are selected from the following combinations of stx1-specific and stx2-specific oligomer pairs: (A) the amplification oligomer pairs of (1-i) and (2-i); (B) the amplification oligomer pairs of (1-i) and (2-ii); (C) the amplification oligomer pairs of (1-ii) and (2-i); (D) the amplification oligomer pairs of (1-iv) and (2-iv); (E) the amplification oligomer pairs of (1-v) and (2-i); and (F) the amplification oligomer pairs of (1-v) and (2-iv). In some such variations, for the combination of stx1-specific and stx2-specific oligomer pairs of (A), the stx1-specific probe has at least 90%, at least 95%, or 100% sequence identity to SEQ ID NO:32 and the stx2-specific probe has at least 90%, at least 95%, or 100% sequence identity to SEQ ID NO:35; for the combination of stx1-specific and stx2-specific oligomer pairs of (B), the stx1-specific probe has at least 90%, at least 95%, or 100% sequence identity to SEQ ID NO:32 and the stx2-specific probe has at least 90%, at least 95%, or 100% sequence identity to SEQ ID NO:42; for the combination of stx1-specific and stx2-specific oligomer pairs of (C), the sod-specific probe has at least 90%, at least 95%, or 100% sequence identity to SEQ ID NO:5 and the stx2-specific probe has at least 90%, at least 95%, or 100% sequence identity to SEQ ID NO:35; for the combination of stx1-specific and stx2-specific oligomer pairs of (D), the stx1-specific probe has at least 90%, at least 95%, or 100% sequence identity to SEQ ID NO:14 and the stx2-specific probe has at least 90%, at least 95%, or 100% sequence identity to SEQ ID NO:49; for the combination of stx1-specific and stx2-specific oligomer pairs of (E), the stx1-specific probe has at least 90%, at least 95%, or 100% sequence identity to SEQ ID NO:22 and the stx2-specific probe has at least 90%, at least 95%, or 100% sequence identity to SEQ ID NO:35; or for the combination of stx1-specific and stx2-specific oligomer pairs of (F), the stx1-specific probe has at least 90%, at least 95%, or 100% sequence identity to SEQ ID NO:22 and the stx2-specific probe has at least 90%, at least 95%, or 100% sequence identity to SEQ ID NO:49.

In certain embodiments of a primer-probe set as above, the primer-probe set further includes an internal control system for verifying reaction conditions. The internal control system typically comprises a control template polynucleotide, a pair of control amplification oligomers, and a control probe. In particular variations, the pair of control amplification oligomers includes a first oligomer having at least 90%, at least 95%, or 100% sequence identity to SEQ ID NO:53 and a second oligomer having at least 90%, at least 95%, or 100% sequence identity to SEQ ID NO:54. In some such variations, the control probe is an oligomer having at least 90%, at least 95%, or 100% sequence identity to SEQ ID NO:55.

In still another aspect, the present invention provides a kit for identification of at least one of a stx1 gene and a stx2 gene, the kit comprising a primer-probe as set forth above.

DETAILED DESCRIPTION OF EMBODIMENTS

Definitions

To aid in understanding aspects of the disclosure, some terms used herein are described in more detail. All other scientific and technical terms used herein have the same meaning as commonly understood by those skilled in the relevant art, such as may be provided in *Dictionary of Microbiology and Molecular Biology*, 2nd ed. (Singleton et al., 1994, John Wiley & Sons, New York, N.Y.), *The Harper Collins Dictionary of Biology* (Hale & Marham, 1991, Harper Perennial, New York, N.Y.), and references cited herein. Unless mentioned otherwise, the techniques employed or contemplated herein are standard methods well known to a person of ordinary skill in the art of molecular biology.

It is to be noted that the term "a" or "an" entity refers to one or more of that entity; for example, "a nucleic acid," is understood to represent one or more nucleic acids. As such, the terms "a" (or "an"), "one or more," and "at least one" can be used interchangeably herein.

Sample. A "sample" or "specimen," including "biological" or "clinical" samples may contain or may be suspected of containing STEC or components thereof, such as nucleic acids or fragments of nucleic acids. A sample may be a complex mixture of components. Samples include "biological samples" which include any tissue or material derived from a living or dead mammal or organism, including, for example, stool, blood, plasma, serum, blood cells, saliva, mucous and cerebrospinal fluid. Samples may also include samples of in vitro cell culture constituents including, for example, conditioned media resulting from the growth of cells and tissues in culture medium. The sample may be treated to chemically, physically or mechanically to disrupt tissue or cell structure to release intracellular nucleic acids into a solution which may contain enzymes, buffers, salts, detergents and the like, to prepare the sample for analysis. In one step of the methods described herein, a sample is provided that is suspected of containing at least one STEC target nucleic acid. Accordingly, this step excludes the physical step of obtaining the sample from a subject.

Polynucleotide. The term denotes a nucleic acid chain. Throughout this application, sequences of polynucleotides are expressed in a direction extending from the 5'-terminus to the 3'-terminus. Standard nucleic acids, e.g., DNA and RNA, are typically synthesized in the 3'-to-5' direction by the addition of nucleotides to the 5'-terminus of a growing nucleic acid.

Nucleotide. This is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of RNA or DNA.

Nucleic Acid. This refers to a multimeric compound comprising two or more covalently bonded nucleotides or nucleotide analogs having nitrogenous heterocyclic bases, or base analogs, where the nucleotides are linked together by phosphodiester bonds or other linkages to form a polynucleotide. Nucleic acids include RNA, DNA, or chimeric DNA-RNA polymers, and analogs thereof. A nucleic acid "backbone" may be made up of a variety of linkages, including one or more of sugar-phosphodiester linkages, peptidenucleic acid bonds, phosphorothioate linkages, methylphosphonate linkages, or combinations thereof. Sugar moieties of the nucleic acid may be either ribose or deoxyribose, or similar compounds having known substitutions, e.g., 2'-methoxy substitutions and 2'-halide substitutions. Nitrogenous bases may be conventional bases (A, G, C, T, U), analogs thereof (e.g., inosine, 5-methylisocytosine, isoguanine; (*The Biochemistry of the Nucleic Acids* 5-36, Adams et al., ed., 11$^{th}$ ed., 1992, Abraham et al., 2007, BioTechniques 43: 617-24)), which include derivatives of purine or pyrimidine bases. Nucleic acids may include "abasic" residues in which the backbone does not include a nitrogenous base for one or more residues (see, for example U.S. Pat. No. 5,585,481, which is incorporated herein by reference in entirety). Nucleic acids may include "locked nucleic acids" (LNA), in which one or more nucleotide monomers have a bicyclic furanose unit locked in an RNA-mimicking sugar conformation, which enhances hybridization affinity toward complementary sequences (Vester et al., 2004, *Biochemistry* 43(42):13233-41). Nucleic acids may include modified bases to alter the function or behaviour of the nucleic acid, e.g., addition of a 3'-terminal dideoxynucleotide to block additional nucleotides from being added to the nucleic acid. Synthetic methods for making nucleic acids in vitro are well known in the art although nucleic acids may be purified from natural sources using routine techniques.

Non-Nucleotide unit. This is a unit that does not significantly participate in hybridization of a polymer. Such units do not, for example, participate in any significant hydrogen bonding with a nucleotide, and would exclude units having, as a component, one of the five canonical nucleotide bases or analogs thereof.

Target nucleic acid. This is a nucleic acid comprising a "target sequence" to be amplified. Target nucleic acids may be DNA or RNA and may be either single-stranded or double-stranded. In a preferred embodiment of the invention, the target nucleic acid is DNA. The target nucleic acid may include other sequences besides the target sequence that may be amplified. Typical target nucleic acids are the STEC genome or are derived from regions of the STEC genome.

Target sequence or target nucleic acid sequence. This term refers to the particular nucleotide sequence of the target nucleic acid that is to be amplified and/or detected. Where the target nucleic acid is originally single-stranded, the term "target sequence" will also refer to the sequence complementary to the target sequence as present in the target nucleic acid. Where the target nucleic acid is originally double-stranded, the term "target sequence" refers to both the sense (+) and antisense (−) strands. In choosing a target sequence, the skilled artisan will understand that a sequence should be chosen so as to distinguish between unrelated or closely related target nucleic acids. The terms "target(s) a sequence" or "target(s) a target nucleic acid" as used herein in reference to a region of STEC nucleic acid refer to a process whereby an oligonucleotide stably hybridizes to the target sequence in a manner that allows for amplification and/or detection as described herein. In one embodiment, the oligonucleotide is complementary to the targeted STEC nucleic acid sequence and contains no mismatches. In another embodiment, the oligonucleotide is complementary but contains 1; or 2; or 3; or 4; or 5 or more mismatches with the targeted STEC nucleic acid sequence. Preferably, the oligonucleotide that stably hybridizes to the STEC nucleic acid sequence includes at least 10 to 50 contiguous nucleotides complementary to the target sequence. It is understood that at least 10 and as many as 50 is an inclusive range such that 10, 50 and each whole number there between are included. The term "configured to target a sequence" as used herein means that the target hybridizing region of an oligonucleotide is designed to have a polynucleotide sequence that could target a sequence of the referenced STEC region. Such an amplification oligonucleotide is not limited to targeting that sequence only, but is rather useful in a composition, in a kit or in a method for targeting a STEC target nucleic acid, as is described herein. The term "configured to" denotes an actual arrangement of the polynucleotide sequence configuration of the amplification oligonucleotide target hybridizing sequence.

Fragment. This term, as used herein in reference to the STEC targeted nucleic acid sequence, refers to a piece of contiguous nucleic acid. In certain embodiments, the fragment includes contiguous nucleotides from a STEC target nucleic acid, wherein the number of contiguous nucleotides in the fragment is less than that for the entire STEC genome or a gene thereof.

Region. This term refers to a portion of a nucleic acid wherein said portion is smaller than the entire nucleic acid. For example, when the nucleic acid of reference is an oligonucleotide promoter, the term "region" may be used refer to the smaller promoter portion of the entire oligonucleotide. Similarly, and also as example only, when the nucleic acid is a target nucleic acid, the term "region" may be used to refer to a smaller area of the nucleic acid.

Oligonucleotide. This term may be used interchangeably with "oligomer and "oligo" and refers to a nucleic acid having generally less than 1,000 nucleotide (nt) residues. Preferably, an oligonucleotide is 10 nucleobases in length to 100 nucleobases in length. It is understood that these ranges are exemplary only, and it is further understood that an oligonucleotide can have a length that is any whole number included in the range from 10 to 100. Oligonucleotides may be purified from naturally occurring sources, or may be synthesized using any of a variety of well-known enzymatic or chemical methods. The term oligonucleotide does not denote any particular function to the reagent and rather is used generically to refer to all such reagents described herein. An oligonucleotide may have various functions. For example, it may function as a primer, a probe, a target capture oligomer or provide any other known function.

As used herein, an oligonucleotide having a nucleic acid sequence "comprising" or "consisting of" or "consisting essentially of" a sequence selected from a group of specific sequences means that the oligonucleotide has the ability to hybridize to a nucleic acid having the exact complement of one of the listed nucleic acid sequences of the group under stringent hybridization conditions. Though the hybridizing oligonucleotide and the target nucleic acid need not be 100% complementary to one another. An exact complement includes the corresponding DNA or RNA sequence.

Corresponds. As used herein, a nucleic acid "corresponds" to a specified nucleic acid if the nucleic acid is 100% identical or complementary to the specified nucleic acid.

Substantially corresponding to. As used herein, a nucleic acid "substantially corresponding to" a specified nucleic acid sequence, or its complement, means that the oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. Substantially corresponding nucleic acids vary by at least one nucleotide from the specified nucleic acid. This variation may be stated in terms of a percentage of sequence identity or complementarity between the nucleic acid and the specified nucleic acid (e.g., from less than 100% to about 80%). One skilled in the art will understand that the recited ranges include all whole and rational numbers of the range (e.g., 92%, 92.377%, etc).

Amplification oligomer. An "amplification oligomer," which may also be called an "amplification oligonucleotide," is an oligomer, at least the 3'-end of which is complementary to part of a target sequence, and which hybridizes to the target sequence and participates in a nucleic acid amplification reaction. A primer may hybridize specifically to a single species of target nucleic acid. Alternatively, a primer may hybridize to a region of a plurality of target nucleic acids wherein the region is substantially conserved amongst the species. An example of an amplification oligomer is a "primer" that hybridizes to a target nucleic acid and contains a 3'-OH end that is extended by a polymerase in an amplification process. Amplification oligomers include oligonucleotides that comprise a 3'-target hybridizing region and a 5'-region that is not configured for hybridizing the target nucleic acids. Examples of such 5'-regions include, but are not limited to, promoter sequences, tag sequences, barcode sequences and the like. The 3'- and 5'-regions may be directly linked (e.g., a phosphorothioate linkage) or indirectly linked (e.g., a 9-carbon linker). An example of an amplification oligomer comprising a 3' target hybridizing segment and a 5'-non-target-hybridizing segment is a "promoter-based amplification oligomer," which comprises a 5'-promoter sequence for initiating transcription by an appropriate polymerase. Size ranges for amplification oligonucleotides include ranges which include target hybridizing regions that are about 10 nucleotides to about 70 nucleotides long, including all whole numbers between 10 and 70. An amplification oligomer may optionally include modified nucleotides or analogs that are not complementary to a target nucleic acid in a strict A:T/U, G:C sense. Such modified nucleotides or analogs are herein considered mismatched to their corresponding target sequence.

Amplification. This refers to any known procedure for obtaining multiple copies of a target nucleic acid sequence or its complement or fragments thereof. The multiple copies may be referred to as amplicons or amplification products. Known amplification methods include both thermal cycling and isothermal amplification methods. Transcription mediated amplification (TMA), polymerase chain reaction (PCR), replicase-mediated amplification, ligase chain reaction (LCR), strand-displacement amplification (SDA), and transcription-mediated or transcription-associated amplification are non-limiting examples of nucleic acid amplification methods (see for example U.S. Pat. Nos. 4,868,105; 5,124,246; 5,130,238; 5,399,491; 5,437,990; 5,554,516; and 7,374,885; and PCT Pub. Nos. WO 88/01302; WO 88/10315 and WO 95/03430 (TMA); U.S. Pat. No. 4,786,600 (RCA); U.S. Pat. Nos. 5,427,930, 5,516,663 (LCR); and U.S. Pat. Nos. 5,422,252; 5,547,861; and 5,648,211 (SDA), each of which is incorporated herein by reference in entirety). PCR is the preferred amplification method, and is well known in the art. Briefly, PCR amplification uses a DNA polymerase, pairs of primers, and thermal cycling to synthesize multiple copies of two complementary strands from dsDNA or from a cDNA (see for example, U.S. Pat. Nos. 4,683,195, 4,683,202, and 4,800,159, each of which is incorporated herein by reference in entirety).

Real-time amplification. As used herein, the term "real-time amplification" refers to amplification of target nucleic acid that is monitored by real-time detection means. Real-time PCR amplification includes a method and reagents for performing what is commonly referred to as Taqman® PCR (see for example, Holland et al., PNAS 88 (16): 7276-7280 (1991); and Livak et al, U.S. Pat. No. 6,030,787, each of which is incorporated herein by reference in entirety).

Amplicon. This term, which is used interchangeably with the term "amplification product," refers to the nucleic acid molecule generated during an amplification procedure that is complementary or homologous to a sequence contained within the target sequence. These terms can be used to refer to a single strand amplification product, a double strand amplification product or one of the strands of a double strand amplification product.

Probe. A probe, also known as a "detection probe" or "detection oligonucleotide" are terms referring to a nucleic acid oligomer that hybridizes specifically to a target sequence in a nucleic acid, or in an amplified nucleic acid, under conditions that promote hybridization to allow detection of the target sequence or amplified nucleic acid. Probe lengths are preferably in the range from 10 nucleobases to 100 nucleobases, inclusive of all whole numbers therein. Detection may either be direct (e.g., a probe hybridized directly to its target sequence) or indirect (e.g., a probe linked to its target via an intermediate molecular structure). Probes may be DNA, RNA, analogs thereof or combinations thereof and they may be labeled or unlabeled. A probe may comprise target-specific sequences and other sequences that contribute to the three-dimensional conformation of the probe (see for example, U.S. Pat. Nos. 5,118,801; 5,312,728; 6,849,412; 6,835,542; 6,534,274; and 6,361,945; and US Pub. No. 20060068417, each of which are incorporated herein by reference in entirety). Detection probes may comprises a 2'-O-methoxy residue which can result in a higher signal being obtained. In general the term "TagMan® probe" refers to oligonucleotides that contain a fluorescent dye, typically on the 5' base, and a non-fluorescent quenching dye (quencher), typically on the 3' base. When irradiated, the excited fluorescent dye transfers energy to the nearby quenching dye molecule rather than fluorescing, resulting in a non-fluorescent substrate. During amplification, the exonuclease activity of the polymerase cleaves the TagMan® probe to separate the fluorophore from the quencher, thereby allowing an unquenched signal to be emitted from the fluorophore as an indicator of amplification.

Label. As used herein, a "label" refers to a moiety or compound joined directly or indirectly to a probe that is detected or leads to a detectable signal. Direct labeling can occur through bonds or interactions that link the label to the probe, including covalent bonds or non-covalent interactions, e.g. hydrogen bonds, hydrophobic and ionic interactions, or formation of chelates or coordination complexes. Indirect labeling can occur through use of a bridging moiety or "linker" such as a binding pair member, an antibody or additional oligomer, which is either directly or indirectly labeled, and which may amplify the detectable signal. Labels may be detectable in a homogeneous assay in which bound labeled probe in a mixture exhibits a detectable change different from that of an unbound labeled probe. A "homogeneous detectable label" can be detected without physically removing bound from unbound forms of the label or labeled probe (see for example, U.S. Pat. Nos. 5,118,801, 5,283,174, 5,312,728, 5,656,207, and 5,658,737, each of which are incorporated herein by reference in entirety). Labels include any detectable moiety, such as a radionuclide, ligand (such as biotin, avidin), enzyme or enzyme substrate, reactive group, or chromophore (such as a dye, particle, or bead that imparts detectable color), luminescent compound (such as bioluminescent, phosphorescent, or chemiluminescent labels), or fluorophore. Common labels used for TagMan® detection probes include a fluorophore and a quencher. Exemplary fluorophores include FAM, SYBR® Green, VIC, JOE, NED, Cy3, ROX, Texas Red and Cy5 dyes (all well known in the art and readily available from numerous commercial sources). Exemplary quenchers include BHQ, TAMRA and DABCLY (all well known in the art and readily available from numerous commercial sources). Synthesis and methods of attaching labels to nucleic acids and detecting labels are well known (see for example, Sambrook et al., *Molecular Cloning, A Laboratory Manual,* 2nd ed. (Cold Spring Harbor Laboratory Press, Cold Spring Harbor, N.Y., 1989), Chapter 10; U.S. Pat. Nos. 5,658,737, 5,656,207, 5,547,842, 5,283,174, and 4,581,333, each of which is incorporated herein by reference in entirety). More than one label, and more than one type of label, may be present on a particular probe, or detection may use a mixture of probes in which each probe is labeled with a compound that produces a different detectable signal (see for example, U.S. Pat. Nos. 6,180,340 and 6,350,579, each of which is incorporated herein by reference in entirety).

Stable. "Stable" or "stable for detection" means that the temperature of a reaction mixture is at least 2° C. below the melting temperature of a nucleic acid duplex.

Capture oligonucleotide. As used herein, a "capture oligonucleotide," "target capture oligonucleotide" or "capture probe" refers to a nucleic acid oligomer that specifically hybridizes to a target sequence in a target nucleic acid by standard base pairing and joins to a binding partner on an immobilized probe to capture the target nucleic acid to a support. One example of a capture oligomer includes an oligonucleotide comprising two binding regions: a target hybridizing region and an immobilized probe-binding region. These two regions may be part of a single contiguous nucleic acid molecule or may be two different oligomers joined together by one or more linkers. A capture oligomer may have a target hybridizing sequence that substantially corresponds to a specific target sequence. Alternatively, a capture oligomer may have a target hybridizing sequence that includes random or non-random poly-GU, poly-GT, or poly U sequences to bind non-specifically to a plurality of nucleic acids, including the target nucleic acid. (PCT Pub No. WO 2008/016988, incorporated herein by reference in entirety). Capture oligomers may include at least one 2' O-methoxy linkage. The immobilized probe binding region can be a nucleic acid sequence, referred to as a tail. Tails include a substantially homopolymeric tail of about 10 to 40 nucleotides (for example, $T_{0-4}A_{10-40}$), or of about 14 to 33 nt (e.g., $T_3A_{14}$ to $T_3A_{30}$), that bind to a complementary immobilized sequence attached to the support particle or support matrix. Thus, a non-limiting example of preferred nucleic acid tails can in some embodiments include $T_{0-4}A_{10-36}$ sequences. Another example of a capture oligomer comprises two regions, a target hybridizing sequence and a binding pair member that is not a nucleic acid sequence (see PCT Pub No. WO 2008/016988 at page 3, lines 2-8 for examples of non-nucleotide binding pairs).

Immobilized oligonucleotide. As used herein, an "immobilized oligonucleotide," "immobilized probe" or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size ±5%), to which an immobilized probe is joined directly (via covalent linkage, chelation, or ionic interaction), or indirectly (via one or more linkers), where the linkage or interaction between the probe and support is stable during hybridization conditions.

Complementary. The term "complementary" means that nucleotide sequences of similar regions of two single-stranded nucleic acids, or to different regions of the same single-stranded nucleic acid have a nucleotide base composition that allow the single-stranded regions to hybridize together in a stable double-stranded hydrogen-bonded region under stringent hybridization or amplification conditions. Sequences that hybridize to each other may be completely complementary or partially complementary to the intended target sequence by standard nucleic acid base pairing (e.g. G:C, A:T or A:U pairing). The term "sufficiently complementary" refers to a contiguous sequence that is capable of hybridizing to another sequence by hydrogen bonding between a series of complementary bases, which may be complementary at each position in the sequence by standard base pairing or may contain one or more residues that are not complementary by standard A:T/U and G:C pairing, or are modified nucleotides such as abasic residues, modified nucleotides or nucleotide analogs. Sufficiently complementary contiguous sequences typically are at least 80% complementary to a sequence to which an oligomer is intended to specifically hybridize (a percentage complementarity range includes all whole and rational numbers of the range). Sequences that are "sufficiently complementary" allow stable hybridization of a nucleic acid oligomer with its target sequence under appropriate hybridization conditions, even if the sequences are not completely complementary.

Preferentially hybridize. The term "preferentially hybridize" means that under stringent hybridization assay conditions, an oligonucleotide hybridizes to its target sequences, or amplicons thereof, to form a stable oligonucleotide: target sequence hybrid, while at the same time, formation of a stable hybrid between an oligonucleotide and a non-target sequence is minimized. For example, a probe oligonucleotide preferentially hybridizes to a target sequence or amplicon thereof to a sufficiently greater extent than to a non-target sequence, to enable detection of the target sequence and amplicon thereof. Appropriate hybridization conditions are well known in the art for probe, amplification, target capture and other oligonucleotides, and may be predicted based on sequence composition, or can be determined by using routine testing methods (see for example Sambrook et al., *Molecular Cloning, A Laboratory Manual*, 2$^{nd}$ ed. (Cold Spring Harbor Laboratory Press, Cold Spring Harbor, N.Y., 1989) at §§ 1.90-1.91, 7.37-7.57, 9.47-9.51 and 11.47-11.57, particularly §§ 9.50-9.51, 11.12-11.13, 11.45-11.47 and 11.55-11.57, incorporated herein by reference in entirety).

Nucleic acid hybrid. The term "nucleic acid hybrid" or "hybrid" or "duplex" refers to a nucleic acid structure containing a double-stranded, hydrogen-bonded region that is at least substantially complementary one to the other, and wherein the duplex is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

Sample preparation. This refers to any steps or methods that treat a sample for subsequent amplification and/or detection of STEC nucleic acids present in the sample. The target nucleic acid may be a minority component in the sample. Sample preparation may include any known method of isolating or concentrating components, such as viruses or nucleic acids using standard microbiology methods. Sample preparation may include physical or mechanical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically captures a target nucleic acid and separates it from other sample components (see for example U.S. Pat. No. 6,110,678 and PCT Pub. No. WO 2008/016988, each of which is incorporated herein by reference in entirety).

Separating, purifying, isolating. These terms mean that one or more components of a sample are removed or separated from other sample components. Sample components include target nucleic acids usually in a generally aqueous solution phase, which may also include cellular fragments, proteins, carbohydrates, lipids, and other nucleic acids. Separating or purifying removes at least 70%, or at least 80%, or at least 95% of the target nucleic acid from other sample components. Ranges of %-purity include all whole and rational numbers of the range.

Specificity. The term "specificity," in the context of an amplification system, is used herein to refer to the characteristic of an amplification system which describes its ability to distinguish between target and non-target sequences dependent on sequence and assay conditions. In terms of nucleic acid amplification, "specificity" generally refers to the ratio of the number of specific amplicons produced to the number of side-products (for example, the signal-to-noise ratio).

Sensitivity. The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction which is characterized, for example, by the ratio of specific amplicons to side-products.

Overview

Nucleic acid oligomer sequences are disclosed that may serve as primers and/or detection probes for amplification and/or detection of nucleic acids derived from Shiga toxin-producing *E. coli* (STEC) or other organisms that produce Shiga toxins. The nucleic acids derived from of Shiga toxin genes may be detected in a sample by using methods of in vitro nucleic acid amplification such as PCR (for example. Taqman® PCR), or transcription-associated amplification—such as TMA or NASBA. Amplification oligomers are configured to specifically hybridize to a Shiga toxin target sequence and generate an amplicon therefrom. Detection probes hybridize specifically to at least a portion of the amplified sequence, either after completion of or during the amplification process. The methods further may use oligonucleotide sequences that serve as capture probes for processing a sample by capturing the target Shiga toxin nucleic acid and separating it from other sample components (see U.S. Pat. Nos. 6,110,678, 6,280,952 and 6,534,273, which are incorporated herein by reference in entirety).

Methods disclosed herein can be used to detect nucleic acids derived from Shiga toxin genes present in samples from or derived from animals and humans.

Compositions disclosed herein include amplification oligomers that can be used to specifically amplify selected nucleic acid sequences present in Shiga toxin genes, and optionally nucleic acid probes for detecting the amplified sequences.

The disclosed nucleic acid sequences and methods are useful for amplifying and detecting nucleic acids from Shiga toxin genes or derived from bacteria present in a sample in a relatively short time so that diagnosis can be made quickly and so that effective treatment can be initiated to limit the spread of the bacteria. Thus, the methods and compositions disclosed herein respond to a need for rapid, sensitive, and specific testing of clinical samples that may contain bacteria with genes encoding Shiga toxins.

The disclosed probe sequences may be used as primers, and the disclosed primers may be used as probes. The same is true for the disclosed probe hybridization regions and primer hybridization regions of a given target gene. Thus, the probe hybridization regions disclosed herein may be used as primer hybridization regions. Likewise, primer hybridization regions disclosed herein may be used as probe hybridization regions.

Oligonucleotides for amplifying a Shiga toxin producing *E. coli* (STEC) target typically comprise at least two amplification oligomers. Some embodiments of the invention may utilise, three, four, five, or even six or ten or more amplification oligomers in, for example, multiplex amplification assays. Thus, by way of example, oligonucleotides for amplifying a Shiga toxin target gene may comprise one, two, three, four, or five or more forward amplification primers and one, two, three, four, or five or more reverse amplification primers. In one embodiment, at least one of the amplification oligomers is configured to specifically hybridize to a region within a target sequence corresponding to the stx1 gene. In another embodiment, at least one of the amplification oligomers is configured to specifically hybridize to a region within a target sequence corresponding to the stx2 gene. In one embodiment, at least two amplification oligomers are used, wherein the amplification oligomers are respectively configured to specifically hybridize to regions within a target sequence selected from the group consisting of stx1 gene and stx2 gene in order to generate an amplicon that can be subsequently detected. Suitably, the amplicon is detectable using a detection probe. Suitably, the amplicon is from 50 to 210 nucleotides in length, including all whole numbers between 50 and 210 that are not explicitly listed here.

In one embodiment, at least one of the amplification oligomers is configured to specifically hybridize to a region within a target sequence of STEC corresponding to nucleotides 2924490-2925716 of GenBank accession number BA000007, GI number 47118301. In one embodiment, at least one of the amplification oligomers is configured to specifically hybridize to a region within a target sequence of STEC corresponding to nucleotides 1266965-1268205 of GenBank accession number BA000007, GI number 47118301. In another embodiment, at least two amplification oligomers are used, wherein the amplification oligomers are configured to specifically hybridize to regions within a target sequence of STEC corresponding to nucleotides 2924490-2925719 of GenBank accession number BA000007, GI number 47118301, in order to generate an amplicon that can be subsequently detected. In another embodiment, at least two amplification oligomers are used, wherein the amplification oligomers are configured to specifically hybridize to regions within a target sequence of STEC corresponding to nucleotides 1266965-1268205 of GenBank accession number BA000007, GI number 47118301, in order to generate an amplicon that can be subsequently detected.

In one embodiment, at least one of the amplification oligomers is configured to specifically hybridize to a region within a target sequence of STEC corresponding to nucleotides 101-246, 346-506, 399-614, 535-663, 568-727, 595-793, 775-898, and 1071-1200 of SEQ ID NO:56. In one embodiment, at least one of the amplification oligomers is configured to specifically hybridize to a region within a target sequence of STEC corresponding to nucleotides 23-131, 387-498, 519-697, 654-748, and 841-1029 of SEQ ID NO:57. In another embodiment, at least two amplification oligomers are used, wherein the amplification oligomers are configured to specifically hybridize to regions within a target sequence of STEC corresponding to nucleotides 101-246, 346-506, 399-614, 535-663, 568-727, 595-793, 775-898, and 1071-1200 of SEQ ID NO:56 in order to generate an amplicon that can be subsequently detected. In another embodiment, at least two amplification oligomers are used, wherein the amplification oligomers are configured to specifically hybridize to regions within a target sequence of STEC corresponding to nucleotides 23-131, 387-498, 519-697, 654-748, and 841-1029 of SEQ ID NO:57 in order to generate an amplicon that can be subsequently detected.

Oligomers for amplifying and/or detecting Shiga toxin target genes (amplification oligomers) include oligonucleotide sequences selected from the group consisting of SEQ ID NOS: 1 to 49 or a combination of two or more thereof. According to one embodiment, at least one first amplification oligomer comprises, consists of or consists essentially of a target hybridizing sequence selected from the group consisting of SEQ ID NOS: 1, 8, 12, 15, 19, 23, 27, 30, 33, 36, 40, 44, or 47 or a combination of two or more thereof. According to one embodiment, at least one second amplification oligomer comprises, consists of consists essentially of a target hybridizing sequence selected from the group consisting of SEQ ID NOS: 2, 6, 9, 13, 16, 20, 24, 28, 31, 34, 37, 41, 45, or 48 or a combination of two or more thereof. Although these sequences are shown as DNA sequences, equivalent RNA sequences can be readily derived by the person skilled in the art and are to be considered as falling within the definition of "oligomers." In addition, complementary sequences of DNA and RNA and reverse complementary sequences can be readily derived by the skilled person. It is therefore to be understood that a description of any individual sequence of DNA, for example, encompasses its complement, its reverse complement and equivalent RNA sequences.

The methods for detecting nucleic acid of a Shiga toxin gene optionally include a detecting step that uses at least one probe that binds specifically to the amplified STEC product (RNA or DNA amplicon, preferably DNA amplicon). In one embodiment, one or more detection probes are configured to detect a sequence in a region corresponding to part of SEQ ID NO:56. In one embodiment, one or more detection probes are configured to detect a sequence in a region corresponding to part of SEQ ID NO:57. In one embodiment, one or more detection probes is individually configured to detect a sequence in a region corresponding to nucleotides 101-246, 346-506, 399-614, 535-663, 568-727, 595-793, 775-898, and 1071-1200 of SEQ ID NO:56. In another embodiment, one or more detection probes are configured to detect a sequence in a region corresponding to nucleotides 23-131, 387-498, 519-697, 654-748, and 841-1029 of SEQ ID NO:57. Probes for the specific detection of STEC sequences include oligomers selected from the group consisting of SEQ ID Nos. 3, 4, 5, 7, 10, 11, 14, 17, 18, 21, 22, 25, 26, 29, 32, 35, 38, 39, 42, 43, 46, 49, or a combination of two or more thereof.

Oligonucleotides for amplifying and detecting the STEC target typically comprise at least two amplification oligomers and at least one probe. Some embodiments of the invention may utilise four, five, six, seven, eight or more amplification oligomers and two, three, four, five or even six or more probes. Thus, by way of example, oligonucleotides for amplifying and detecting a Shiga toxin gene target may comprise two or three or more forward amplification primers together with two or three or more reverse amplification primers together with two, three, four, five or even six or more probes.

Assays for detection of a Shiga toxin gene may include an internal control (IC) nucleic acid that is amplified and detected by using IC-specific primers and probe in the same reaction mixtures used for amplification and detection of a region of a Shiga toxin gene. Amplification and detection of the IC-specific sequence demonstrates that assay reagents and conditions were properly used even when a signal specific for a Shiga toxin gene is not detected for a tested sample (i.e., negative samples). The IC may be used as an internal calibrator for the assay that provides a quantitative result. The IC may be a randomized sequence derived from a naturally occurring source bacterium that does not harbor a Shiga toxin gene. An example of an IC-specific primer-probe set is SEQ ID NO:53 (forward), SEQ ID NO:54 (reverse) and SEQ ID NO:55 (probe).

Combinations of amplification oligomers specific for identification of a Shiga toxin gene are therefore contemplated. Each member of the combination may have at least 90% sequence identity to 100% sequence identity to any of the SEQ ID NOs of the amplification oligomers described herein. For greater clarity, each member of a combination of amplification oligomers may have at least 90%, at least 91%, at least 92%, at least 93%, at least 94%, at least 95%, at least 96%, at least 97%, at least 98%, at least 99% or 100% sequence identity with the SEQ ID NOs of the amplification oligomers described herein.

According to one embodiment, at least one first amplification oligomer comprising, consisting of, or consisting essentially of a target hybridizing sequence with at least 90% sequence identity to SEQ ID NO:1 is used in combination with at least one second amplification oligomer comprising, consisting of, or consisting essentially of a target hybridizing sequence with at least 90% sequence identity to SEQ ID NO:2, SEQ ID NO:3, SEQ ID NO:4, SEQ ID NO:5, SEQ ID NO:6, or SEQ ID NO:7. In particular variations, at least one first amplification oligomer comprising, consisting of, or consisting essentially of a target hybridizing sequence with at least 90% sequence identity to SEQ ID NO:1 is used in combination with at least one second amplification oligomer comprising, consisting of, or consisting essentially of a target hybridizing sequence with at least 90% sequence identity to SEQ ID NO:2. In other variations, at least one first amplification oligomer comprising, consisting of, or consisting essentially of a target hybridizing sequence with at least 90% sequence identity to SEQ ID NO:1 is used in combination with at least one second amplification oligomer comprising, consisting of, or consisting essentially of a target hybridizing sequence with at least 90% sequence identity to SEQ ID NO:6.

According to another embodiment, at least one first amplification oligomer comprising, consisting of, or consisting essentially of a target hybridizing sequence with at least 90% sequence identity to SEQ ID NO:8 is used in combination with at least one second amplification oligomer comprising, consisting of, or consisting essentially of a target hybridizing sequence with at least 90% sequence identity to SEQ ID NO:9, SEQ ID NO:10, or SEQ ID NO:11. In particular variations, at least one first amplification oligomer comprising, consisting of, or consisting essentially of a target hybridizing sequence with at least 90% sequence identity to SEQ ID NO:8 is used in combination with at least one second amplification oligomer comprising, consisting of, or consisting essentially of a target hybridizing sequence with at least 90% sequence identity to SEQ ID NO:9.

According to another embodiment, at least one first amplification oligomer comprising, consisting of, or consisting essentially of a target hybridizing sequence as with at least 90% sequence identity to SEQ ID NO:12 is used in combination with at least one second amplification oligomer comprising, consisting of, or consisting essentially of a target hybridizing sequence with at least 90% sequence identity to SEQ ID NO:13 or SEQ ID NO:14. In particular variations, at least one first amplification oligomer comprising, consisting of, or consisting essentially of a target hybridizing sequence as with at least 90% sequence identity to SEQ ID NO:12 is used in combination with at least one second amplification oligomer comprising, consisting of, or consisting essentially of a target hybridizing sequence with at least 90% sequence identity to SEQ ID NO:13.

According to another embodiment, at least one first amplification oligomer comprising, consisting of, or consisting essentially of a target hybridizing sequence with at least 90% sequence identity to SEQ ID NO:15 is used in combination with at least one second amplification oligomer comprising, consisting of, or consisting essentially of a target hybridizing sequence with at least 90% sequence identity to SEQ ID NO:16, SEQ ID NO:17, or SEQ ID NO:18. In particular variations, at least one first amplification oligomer comprising, consisting of, or consisting essentially of a target hybridizing sequence with at least 90% sequence identity to SEQ ID NO:15 is used in combination with at least one second amplification oligomer comprising, consisting of, or consisting essentially of a target hybridizing sequence with at least 90% sequence identity to SEQ ID NO:16.

According to one embodiment, at least one first amplification oligomer comprising, consisting of, or consisting essentially of a target hybridizing sequence with at least 90% sequence identity to SEQ ID NO:19 is used in combination with at least one second amplification oligomer comprising, consisting of, or consisting essentially of a target hybridizing sequence with at least 90% sequence identity to SEQ ID NO:20, SEQ ID NO:21, or SEQ ID NO:22. In particular variations, at least one first amplification oligomer comprising, consisting of, or consisting essentially of a target hybridizing sequence with at least 90% sequence identity to SEQ ID NO:19 is used in combination with at least one second amplification oligomer comprising, consisting of, or consisting essentially of a target hybridizing sequence with at least 90% sequence identity to SEQ ID NO:20.

According to another embodiment, at least one first amplification oligomer comprising, consisting of, or consisting essentially of a target hybridizing sequence with at least 90% sequence identity to SEQ ID NO:23 is used in combination with at least one second amplification oligomer comprising, consisting of, or consisting essentially of a target hybridizing sequence with at least 90% sequence identity to SEQ ID NO:24, SEQ ID NO:25, SEQ ID NO:26. In particular variations, at least one first amplification oligomer comprising, consisting of, or consisting essentially of a target hybridizing sequence with at least 90% sequence identity to SEQ ID NO:23 is used in combination with at least one second amplification oligomer comprising, consisting of, or consisting essentially of a target hybridizing sequence with at least 90% sequence identity to SEQ ID NO:24.

According to one embodiment, at least one first amplification oligomer comprising, consisting of, or consisting essentially of a target hybridizing sequence with at least 90% sequence identity to SEQ ID NO:27 is used in combination with at least one second amplification oligomer comprising, consisting of, or consisting essentially of a target hybridizing sequence with at least 90% sequence identity to SEQ ID NO:28 or SEQ ID NO:29. In particular variations, at least one first amplification oligomer comprising, consisting of, or consisting essentially of a target hybridizing sequence with at least 90% sequence identity to SEQ ID NO:27 is used in combination with at least one second amplification oligomer comprising, consisting of, or consisting essentially of a target hybridizing sequence with at least 90% sequence identity to SEQ ID NO:28.

According to one embodiment, at least one first amplification oligomer comprising, consisting of, or consisting essentially of a target hybridizing sequence with at least 90% sequence identity to SEQ ID NO:30 is used in combination with at least one second amplification oligomer comprising, consisting of, or consisting essentially of a target hybridizing sequence with at least 90% sequence identity to SEQ ID NO:31 or SEQ ID NO:32. In particular variations, at least one first amplification oligomer comprising, consisting of, or consisting essentially of a target hybridizing sequence with at least 90% sequence identity to SEQ ID NO:30 is used in combination with at least one second amplification oligomer comprising, consisting of, or consisting essentially of a target hybridizing sequence with at least 90% sequence identity to SEQ ID NO:31.

According to one embodiment, at least one first amplification oligomer comprising, consisting of, or consisting essentially of a target hybridizing sequence with at least 90% sequence identity to SEQ ID NO:33 is used in combination with at least one second amplification oligomer comprising, consisting of, or consisting essentially of a target hybridizing sequence with at least 90% sequence identity to SEQ ID NO:34 or SEQ ID NO:35. In particular variations, at least one first amplification oligomer comprising, consisting of, or consisting essentially of a target hybridizing sequence with at least 90% sequence identity to SEQ ID NO:33 is used in combination with at least one second amplification oligomer comprising, consisting of, or consisting essentially of a target hybridizing sequence with at least 90% sequence identity to SEQ ID NO:34.

According to one embodiment, at least one first amplification oligomer comprising, consisting of, or consisting essentially of a target hybridizing sequence with at least 90% sequence identity to SEQ ID NO:36 is used in combination with at least one second amplification oligomer comprising, consisting of, or consisting essentially of a target hybridizing sequence with at least 90% sequence identity to SEQ ID NO:37, SEQ ID NO:38, or SEQ ID NO:39. In particular variations, at least one first amplification oligomer comprising, consisting of, or consisting essentially of a target hybridizing sequence with at least 90% sequence identity to SEQ ID NO:36 is used in combination with at least one second amplification oligomer comprising, consisting of, or consisting essentially of a target hybridizing sequence with at least 90% sequence identity to SEQ ID NO:37.

According to one embodiment, at least one first amplification oligomer comprising, consisting or consisting essentially of a target hybridizing sequence with at least 90% sequence identity to SEQ ID NO:40 is used in combination with at least one second amplification oligomer comprising, consisting of, or consisting essentially of a target hybridizing sequence with at least 90% sequence identity to SEQ ID NO:41, SEQ ID NO:42, or SEQ ID NO:43. In particular variations, at least one first amplification oligomer comprising, consisting or consisting essentially of a target hybridizing sequence with at least 90% sequence identity to SEQ ID NO:40 is used in combination with at least one second amplification oligomer comprising, consisting of, or consisting essentially of a target hybridizing sequence with at least 90% sequence identity to SEQ ID NO:41.

According to one embodiment, at least one first amplification oligomer comprising, consisting of, or consisting essentially of a target hybridizing sequence with at least 90% sequence identity to SEQ ID NO:44 is used in combination with at least one second amplification oligomer comprising, consisting of, or consisting essentially of a target hybridizing sequence with at least 90% sequence identity to SEQ ID NO:45 or SEQ ID NO:46. In particular variations, at least one first amplification oligomer comprising, consisting of, or consisting essentially of a target hybridizing sequence with at least 90% sequence identity to SEQ ID NO:44 is used in combination with at least one second amplification oligomer comprising, consisting of, or consisting essentially of a target hybridizing sequence with at least 90% sequence identity to SEQ ID NO:45.

According to one embodiment, at least one first amplification oligomer comprising, consisting of, or consisting essentially of a target hybridizing sequence with at least 90% sequence identity to SEQ ID NO:47 is used in combination with at least one second amplification oligomer comprising, consisting of, or consisting essentially of a target hybridizing sequence with at least 90% sequence identity to SEQ ID NO:48 or SEQ ID NO:49. In particular variations, at least one first amplification oligomer comprising, consisting of, or consisting essentially of a target hybridizing sequence with at least 90% sequence identity to SEQ ID NO:47 is used in combination with at least one second amplification oligomer comprising, consisting of, or consisting essentially of a target hybridizing sequence with at least 90% sequence identity to SEQ ID NO:48.

According to one embodiment, at least one first amplification oligomer comprising, consisting of, or consisting essentially of a target hybridizing sequence with at least 90% sequence identity to SEQ ID NO:50 is used in combination with at least one second amplification oligomer comprising, consisting of, or consisting essentially of a target hybridizing sequence with at least 90% sequence identity to SEQ ID NO:51 or SEQ ID NO:52. In particular variations, at least one first amplification oligomer comprising, consisting of, or consisting essentially of a target hybridizing sequence with at least 90% sequence identity to SEQ ID NO:50 is used in combination with at least one second amplification oligomer comprising, consisting of, or consisting essentially of a target hybridizing sequence with at least 90% sequence identity to SEQ ID NO:51.

According to one embodiment, at least one first amplification oligomer comprising, consisting of, or consisting essentially of a target hybridizing sequence with at least 90% sequence identity to SEQ ID NO:53 is used in combination with at least one second amplification oligomer comprising, consisting of, or consisting essentially of a target hybridizing sequence with at least 90% sequence identity to SEQ ID NO:54 or SEQ ID NO:55. In particular variations, at least one first amplification oligomer comprising, consisting of, or consisting essentially of a target hybridizing sequence with at least 90% sequence identity to SEQ ID NO:53 is used in combination with at least one second amplification oligomer comprising, consisting of, or consisting essentially of a target hybridizing sequence with at least 90% sequence identity to SEQ ID NO:54.

Combinations of oligomers and probes that can be used for the amplification and detection of multiple STEC targets are also disclosed.

In one embodiment, two amplification oligomers and one probe are configured to specifically hybridize to a region within a target sequence of a Shiga toxin gene corresponding to nucleotides 101-246, 346-506, 399-614, 535-663, 568-727, 595-793, 775-898 or 1071-1200 of SEQ ID NO:56. In one embodiment, two amplification oligomers and one probe are configured to specifically hybridize to a region within a target sequence of a Shiga toxin gene corresponding to nucleotides 23-131, 387-498, 519-697, 654-748 or 841-1029 of SEQ ID NO:57.

Each probe in the primer-probe combinations for identification of a Shiga toxin gene described herein may have at least 90% sequence identity to 100% sequence identity to any of the SEQ ID NOs of the probes described herein. For greater clarity, each probe in a primer-probe combination may have at least 90%, at least 91%, at least 92%, at least 93%, at least 94%, at least 95%, at least 96%, at least 97%, at least 98%, at least 99% or 100% sequence identity with the SEQ ID Nos of the probes described herein.

In one embodiment, at least one first amplification oligomer comprising, consisting of, or consisting essentially of a target hybridizing sequence with at least 90% sequence identity to SEQ ID NO:1 is used in combination with at least one second amplification oligomer comprising, consisting of, or consisting essentially of a target hybridizing sequence with at least 90% sequence identity to SEQ ID NO:2, and is used in combination with at least one probe comprising, consisting of consisting essentially of a target hybridizing sequence with at least 90% sequence identity to SEQ ID NO:3, SEQ ID NO:4, or SEQ ID NO:5; or a sequence with at least 90% sequence identity to SEQ ID NO:1 is used in combination with at least one second amplification oligomer comprising, consisting of, or consisting essentially of a target hybridizing sequence with at least 90% sequence identity to SEQ ID NO:6, and is used in combination with at least one probe comprising, consisting of, or consisting essentially of a target hybridizing sequence with at least 90% sequence identity to SEQ ID NO:4 or SEQ ID NO:7.

In one embodiment, at least one first amplification oligomer comprising, consisting of, or consisting essentially of a target hybridizing sequence with at least 90% sequence identity to SEQ ID NO:8 is used in combination with at least one second amplification oligomer comprising, consisting of, or consisting essentially of a target hybridizing sequence with at least 90% sequence identity to SEQ ID NO:9, and is used in combination with at least one probe comprising, consisting of, of consisting essentially of a target hybridizing sequence with at least 90% sequence identity to SEQ ID NO:10 or SEQ ID NO:11.

In one embodiment, at least one first amplification oligomer comprising, consisting of, or consisting essentially of a target hybridizing sequence with at least 90% sequence identity to SEQ ID NO:12 is used in combination with at least one second amplification oligomer comprising, consisting of, or consisting essentially of a target hybridizing sequence with at least 90% sequence identity to SEQ ID NO:13, and is used in combination with at least one probe comprising, consisting of, or consisting essentially of a target hybridizing sequence with at least 90% sequence identity to SEQ ID NO:14.

In one embodiment, at least one first amplification oligomer comprising, consisting of, or consisting essentially of a target hybridizing sequence with at least 90% sequence identity to SEQ ID NO:15 is used in combination with at least one second amplification oligomer comprising, consisting of, or consisting essentially of a target hybridizing sequence with at least 90% sequence identity to SEQ ID NO:16, and is used in combination with at least one probe comprising, consisting of, or consisting essentially of a target hybridizing sequence with at least 90% sequence identity to SEQ ID NO:17 or SEQ ID NO:18.

In one embodiment, at least one first amplification oligomer comprising, consisting of, or consisting essentially of a target hybridizing sequence with at least 90% sequence identity to SEQ ID NO:19 is used in combination with at least one second amplification oligomer comprising, consisting of, or consisting essentially of a target hybridizing sequence with at least 90% sequence identity to SEQ ID NO:20, and is used in combination with at least one probe comprising, consisting of, or consisting essentially of a target hybridizing sequence with at least 90% sequence identity to SEQ ID NO:21 or SEQ ID NO:22.

In one embodiment, at least one first amplification oligomer comprising, consisting of, or consisting essentially of a target hybridizing sequence with at least 90% sequence identity to SEQ ID NO:23 is used in combination with at least one second amplification oligomer comprising, consisting of, or consisting essentially of a target hybridizing sequence with at least 90% sequence identity to SEQ ID NO:24, and is used in combination with at least one probe comprising, consisting of, or consisting essentially of a target hybridizing sequence with at least 90% sequence identity to SEQ ID NO:25 or SEQ ID NO:26.

In one embodiment, at least one first amplification oligomer comprising, consisting of, or consisting essentially of a target hybridizing sequence with at least 90% sequence identity to SEQ ID NO:27 is used in combination with at least one second amplification oligomer comprising, consisting of, or consisting essentially of a target hybridizing sequence with at least 90% sequence identity to SEQ ID NO:28, and is used in combination with at least one probe comprising, consisting of, or consisting essentially of a target hybridizing sequence with at least 90% sequence identity to SEQ ID NO:29.

In one embodiment, at least one first amplification oligomer comprising, consisting of, or consisting essentially of a target hybridizing sequence with at least 90% sequence identity to SEQ ID NO:30 is used in combination with at least one second amplification oligomer comprising, consisting of, or consisting essentially of a target hybridizing sequence with at least 90% sequence identity to SEQ ID NO:31 is used in combination with at least one probe comprising, consisting of, or consisting essentially of a target hybridizing sequence with at least 90% sequence identity to SEQ ID NO:32.

In one embodiment, at least one first amplification oligomer comprising, consisting of, or consisting essentially of a target hybridizing sequence with at least 90% sequence identity to SEQ ID NO:33 is used in combination with at least one second amplification oligomer comprising, consisting of, or consisting essentially of a target hybridizing sequence with at least 90% sequence identity to SEQ ID NO:34, and is used in combination with at least one probe comprising, consisting of, or consisting essentially of a target hybridizing sequence with at least 90% sequence identity to SEQ ID NO:35.

In one embodiment, at least one first amplification oligomer comprising, consisting of, or consisting essentially of a target hybridizing sequence with at least 90% sequence identity to SEQ ID NO:36 is used in combination with at least one second amplification oligomer comprising, consisting of, or consisting essentially of a target hybridizing sequence with at least 90% sequence identity to SEQ ID NO:37, and is used in combination with at least one probe comprising, consisting of, or consisting essentially of a target hybridizing sequence with at least 90% sequence identity to SEQ ID NO:38 or SEQ ID NO:39.

In one embodiment, at least one first amplification oligomer comprising, consisting of, or consisting essentially of a target hybridizing sequence with at least 90% sequence identity to SEQ ID NO:40 is used in combination with at least one second amplification oligomer comprising, consisting of, or consisting essentially of a target hybridizing sequence with at least 90% sequence identity to SEQ ID NO:41, and is used in combination with at least one probe comprising, consisting of, or consisting essentially of a target hybridizing sequence with at least 90% sequence identity to SEQ ID NO:42 or SEQ ID NO:43.

In one embodiment, at least one first amplification oligomer comprising, consisting of, or consisting essentially of a target hybridizing sequence with at least 90% sequence identity to SEQ ID NO:44 is used in combination with at least one second amplification oligomer comprising, consisting of, or consisting essentially of a target hybridizing sequence with at least 90% sequence identity to SEQ ID NO:45, and is used in combination with at least one probe comprising, consisting of, or consisting essentially of a target hybridizing sequence with at least 90% sequence identity to SEQ ID NO:46.

In one embodiment, at least one first amplification oligomer comprising, consisting of, or consisting essentially of a target hybridizing sequence with at least 90% sequence identity to SEQ ID NO:47 is used in combination with at least one second amplification oligomer comprising, consisting of, or consisting essentially of a target hybridizing sequence with at least 90% sequence identity to SEQ ID NO:48, and is used in combination with at least one probe comprising, consisting of, or consisting essentially of a target hybridizing sequence with at least 90% sequence identity to SEQ ID NO:49.

In one embodiment, at least one first amplification oligomer comprising, consisting of, or consisting essentially of a target hybridizing sequence with at least 90% sequence identity to SEQ ID NO:50 is used in combination with at least one second amplification oligomer comprising, consisting of, or consisting essentially of a target hybridizing sequence with at least 90% sequence identity to SEQ ID NO:51, and is used in combination with at least one probe comprising, consisting of, or consisting essentially of a target hybridizing sequence with at least 90% sequence identity to SEQ ID NO:52.

In one embodiment, at least one first amplification oligomer comprising, consisting of, or consisting essentially of a target hybridizing sequence with at least 90% sequence identity to SEQ ID NO:53 is used in combination with at least one second amplification oligomer comprising, consisting of, or consisting essentially of a target hybridizing sequence with at least 90% sequence identity to SEQ ID NO:54, and is used in combination with at least one probe comprising, consisting of, or consisting essentially of a target hybridizing sequence with at least 90% sequence identity to SEQ ID NO:55.

In another embodiment, two different sets of primers and probes configured to hybridize STEC target regions are combined. For convenience, combinations of STEC regions are provided in Table 1. In the description below, the parenthesized letters correspond to STEC target sequences as follows: For a target sequence of a STEC gene corresponding to SEQ ID NO:56, 101-246 (A), 346-506 (B), 399-614 (C), 535-663 (D), 568-727 (E), 595-793 (F), 775-898 (G) and 1071-1200 (H); and for a target sequence of a STEC gene corresponding to SEQ ID NO:57, 23-131 (I), 387-498 (J), 519-697 (K), 654-748 (L) and 841-1029 (M).

In one embodiment, a multiplex comprises at least two amplification oligomers and probe combinations wherein the first amplification oligomers and probe combination comprises, consists, or consists essentially of at least three target hybridizing sequence selected from the group consisting of sequences with at least 90% sequence identity to SEQ ID NO:1, SEQ ID NO:2, SEQ ID NO:3, SEQ ID NO:4, and SEQ ID NO:5 and wherein the second amplification oligomers and probe combination comprises, consists, or consists essentially of: at least three target hybridizing sequences selected from the group consisting of sequences with at least 90% sequence identity to SEQ ID NO:8, SEQ ID NO:9, SEQ ID NO:10, and SEQ ID NO:11; at least three target hybridizing sequences selected from the group consisting of sequences with at least 90% sequence identity to SEQ ID NO:12, SEQ ID NO:13, and SEQ ID NO:14; at least three target hybridizing sequences selected from the group consisting of sequences with at least 90% sequence identity to SEQ ID NO:15, SEQ ID NO:16, SEQ ID NO:17, and SEQ ID NO:18; at least three target hybridizing sequences selected from the group consisting of sequences with at least 90% sequence identity to SEQ ID NO:19, SEQ ID NO:20, SEQ ID NO:21, and SEQ ID NO:22; at least three target hybridizing sequences selected from the group consisting of sequences with at least 90% sequence identity to SEQ ID NO:23, SEQ ID NO:24, SEQ ID NO:25, and SEQ ID NO:26; at least three target hybridizing sequences selected from the group consisting of sequences with at least 90% sequence identity to SEQ ID NO:27, SEQ ID NO:28, and SEQ ID NO:29; at least three target hybridizing sequences selected from the group consisting of sequences with at least 90% sequence identity to SEQ ID NO:30, SEQ ID NO:31, and SEQ ID NO:32; at least three target hybridizing sequences selected from the group consisting of sequences with at least 90% sequence identity to SEQ ID NO:33, SEQ ID NO:34, and SEQ ID NO:35; at least three target hybrid-

TABLE 1

|   | A  | B  | C  | D  | E  | F  | G  | H  | I  | J  | K  | L  | M  |
|---|----|----|----|----|----|----|----|----|----|----|----|----|----|
| A | AA | AB | AC | AD | AE | AF | AG | AH | AI | AJ | AK | AL | AM |
| B | BA | BB | BC | BD | BE | BF | BG | BH | BI | BJ | BK | BL | BM |
| C | CA | CB | CC | CD | CE | CF | CG | CH | CI | CJ | CK | CL | CM |
| D | DA | DB | DC | DD | DE | DF | DG | DH | DI | DJ | DK | DL | DM |
| E | EA | EB | EC | ED | EE | EF | EG | EH | EI | EJ | EK | EL | EM |
| F | FA | FB | FC | FD | FE | FF | FG | FH | FI | FJ | FK | FL | FM |
| G | GA | GB | GC | GD | GE | GF | GG | GH | GI | GJ | GK | GL | GM |
| H | HA | HB | HC | HD | HE | HF | HG | HH | HI | HJ | HK | HL | HM |
| I | IA | IB | IC | ID | IE | IF | IG | IH | II | IJ | IK | IL | IM |
| J | JA | JB | JC | JD | JE | JF | JG | JH | JI | JJ | JK | JL | JM |
| K | KA | KB | KC | KD | KE | KF | KG | KH | KI | KJ | KK | KL | KM |
| L | LA | LB | LC | LD | LE | LF | LG | LH | LI | LJ | LK | LL | LM |
| M | MA | MB | MC | MD | ME | MF | MG | MH | MI | MJ | MK | ML | MM |

Thus in Table 1, an embodiment of two different sets of primers and probes configured to hybridize STEC target sequences shown as BM, means that one set of primers and probe are configured to hybridize STEC target sequence B (corresponding to nucleotides 346-506 of SEQ ID NO:56) and the second set of primers and probe are configured to hybridize STEC target sequence M (corresponding to nucleotides 841-1029 of SEQ ID NO:57). Embodiments of two different sets of primers and probes configured to hybridize STEC target sequences shown in Table 1 using the same letter (e.g. AA) means that the first and second primer/probe sets are both configured to target the same region (in this example, a region corresponding to nucleotides 101-246 of SEQ ID NO:56) but the first primer/probe set is different than the second primer probe set.

izing sequences selected from the group consisting of sequences with at least 90% sequence identity to SEQ ID NO:36, SEQ ID NO:37, SEQ ID NO:28, and SEQ ID NO:39; at least three target hybridizing sequences selected from the group consisting of sequences with at least 90% sequence identity to SEQ ID NO:40, SEQ ID NO:41, SEQ ID NO:42, and SEQ ID NO:43; at least three target hybridizing sequences selected from the group consisting of sequences with at least 90% sequence identity to SEQ ID NO:44, SEQ ID NO:45, and sequences with at least 90% sequence identity to SEQ ID NO:46; or at least three target hybridizing sequences selected from the group consisting of SEQ ID NO:47, SEQ ID NO:48, and SEQ ID NO:49.

In one embodiment, a multiplex comprises at least two amplification oligomers and probe combinations wherein the first amplification oligomers and probe combination comprises, consists, or consists essentially of at least three target hybridizing sequence selected from the group consisting of sequences with at least 90% sequence identity to SEQ ID NO:1, SEQ ID NO:4, SEQ ID NO:6, and SEQ ID NO:7 and wherein the second amplification oligomers and probe combination comprises, consists, or consists essentially of: at least three target hybridizing sequences selected from the group consisting of sequences with at least 90% sequence identity to SEQ ID NO:8, SEQ ID NO:9, SEQ ID NO:10, and SEQ ID NO:11; at least three target hybridizing sequences selected from the group consisting of sequences with at least 90% sequence identity to SEQ ID NO:12, SEQ ID NO:13, and SEQ ID NO:14; at least three target hybridizing sequences selected from the group consisting of sequences with at least 90% sequence identity to SEQ ID NO:15, SEQ ID NO:16, SEQ ID NO:17, and SEQ ID NO:18; at least three target hybridizing sequences selected from the group consisting of sequences with at least 90% sequence identity to SEQ ID NO:19, SEQ ID NO:20, SEQ ID NO:21, and SEQ ID NO:22; at least three target hybridizing sequences selected from the group consisting of sequences with at least 90% sequence identity to SEQ ID NO:23, SEQ ID NO:24, SEQ ID NO:25, and SEQ ID NO:26; at least three target hybridizing sequences selected from the group consisting of sequences with at least 90% sequence identity to SEQ ID NO:27, SEQ ID NO:28, and SEQ ID NO:29; at least three target hybridizing sequences selected from the group consisting of sequences with at least 90% sequence identity to SEQ ID NO:30, SEQ ID NO:31, and SEQ ID NO:32; at least three target hybridizing sequences selected from the group consisting of sequences with at least 90% sequence identity to SEQ ID NO:33, SEQ ID NO:34, and SEQ ID NO:35; at least three target hybridizing sequences selected from the group consisting of sequences with at least 90% sequence identity to SEQ ID NO:36, SEQ ID NO:37, SEQ ID NO:38, and SEQ ID NO:39; at least three target hybridizing sequences selected from the group consisting of sequences with at least 90% sequence identity to SEQ ID NO:40, SEQ ID NO:41, SEQ ID NO:42, and SEQ ID NO:43; at least three target hybridizing sequences selected from the group consisting of sequences with at least 90% sequence identity to SEQ ID NO:44, SEQ ID NO:45, and SEQ ID NO:46; or at least three target hybridizing sequences selected from the group consisting of sequences with at least 90% sequence identity to SEQ ID NO:47, SEQ ID NO:48, and SEQ ID NO:49.

In one embodiment, a multiplex comprises at least two amplification oligomers and probe combinations wherein the first amplification oligomers and probe combination comprises, consists, or consists essentially of at least three target hybridizing sequence selected from the group consisting of sequences with at least 90% sequence identity to SEQ ID NO:12, SEQ ID NO:13, and SEQ ID NO:14 and wherein the second amplification oligomers and probe combination comprises, consists, or consists essentially of: at least three target hybridizing sequences selected from the group consisting of sequences with at least 90% sequence identity to SEQ ID NO:15, SEQ ID NO:16, SEQ ID NO:17, and SEQ ID NO:18; at least three target hybridizing sequences selected from the group consisting of sequences with at least 90% sequence identity to SEQ ID NO:19, SEQ ID NO:20, SEQ ID NO:21, and SEQ ID NO:22; at least three target hybridizing sequences selected from the group consisting of sequences with at least 90% sequence identity to SEQ ID NO:23, SEQ ID NO:24, SEQ ID NO:25, and SEQ ID NO:26; at least three target hybridizing sequences selected from the group consisting of sequences with at least 90% sequence identity to SEQ ID NO:27, SEQ ID NO:28, and SEQ ID NO:29; at least three target hybridizing sequences selected from the group consisting of sequences with at least 90% sequence identity to SEQ ID NO:30, SEQ ID NO:31, and SEQ ID NO:32; at least three target hybridizing sequences selected from the group consisting of sequences with at least 90% sequence identity to SEQ ID NO:33, SEQ ID NO:34, and SEQ ID NO:35; at least three target hybridizing sequences selected from the group consisting of sequences with at least 90% sequence identity to SEQ ID NO:36, SEQ ID NO:37, SEQ ID NO:38, and SEQ ID NO:39; at least three target hybridizing sequences selected from the group consisting of sequences with at least 90% sequence identity to SEQ ID NO:40, SEQ ID NO:41, SEQ ID NO:42, and SEQ ID NO:43; at least three target hybridizing sequences selected from the group consisting of sequences with at least 90% sequence identity to SEQ ID NO:44, SEQ ID NO:45, and SEQ ID NO:46; or at least three target hybridizing sequences selected from the group consisting of sequences with at least 90% sequence identity to SEQ ID NO:47, SEQ ID NO:48, and SEQ ID NO:49.

In one embodiment, a multiplex comprises at least two amplification oligomers and probe combinations wherein the first amplification oligomers and probe combination comprises, consists, or consists essentially of at least three target hybridizing sequence selected from the group consisting of sequences with at least 90% sequence identity to SEQ ID NO:19, SEQ ID NO:20, SEQ ID NO:21, and SEQ ID NO:22 and wherein the second amplification oligomers and probe combination comprises, consists, or consists essentially of: at least three target hybridizing sequences selected from the group consisting of sequences with at least 90% sequence identity to SEQ ID NO:23, SEQ ID NO:24, SEQ ID NO:25, and SEQ ID NO:26; at least three target hybridizing sequences selected from the group consisting of sequences with at least 90% sequence identity to SEQ ID NO:27, SEQ ID NO:28, and SEQ ID NO:29; at least three target hybridizing sequences selected from the group consisting of sequences with at least 90% sequence identity to SEQ ID NO:30, SEQ ID NO:31, and SEQ ID NO:32; at least three target hybridizing sequences selected from the group consisting of sequences with at least 90% sequence identity to SEQ ID NO:33, SEQ ID NO:34, SEQ ID NO:35; at least three target hybridizing sequences selected from the group consisting of sequences with at least 90% sequence identity to SEQ ID NO:36, SEQ ID NO:37, SEQ ID NO:38, and SEQ ID NO:39; at least three target hybridizing sequences selected from the group consisting of sequences with at least 90% sequence identity to SEQ ID NO:40, SEQ ID NO:41, SEQ ID NO:42, and SEQ ID NO:43; at least three target hybridizing sequences selected from the group consisting of sequences with at least 90% sequence identity to SEQ ID NO:44, SEQ ID NO:45, and SEQ ID NO:46; or at least three target hybridizing sequences selected from the group consisting of sequences with at least 90% sequence identity to SEQ ID NO:47, SEQ ID NO:48, and SEQ ID NO:49.

In one embodiment, a multiplex comprises at least two amplification oligomers and probe combinations wherein the first amplification oligomers and probe combination comprises, consists, or consists essentially of at least three target hybridizing sequence selected from the group consisting of sequences with at least 90% sequence identity to SEQ ID NO:23, SEQ ID NO:24, SEQ ID NO:25, and SEQ ID NO:26 and wherein the second amplification oligomers and probe combination comprises, consists, or consists essentially of: at least three target hybridizing sequences selected from the group consisting of sequences with at least 90% sequence identity to SEQ ID NO:27, SEQ ID NO:28, and SEQ ID NO:29; at least three target hybridizing sequences selected from the group consisting of sequences with at least 90% sequence identity to SEQ ID NO:30, SEQ ID NO:31, and SEQ ID NO:32; at least three target hybridizing sequences selected from the group consisting of sequences with at least 90% sequence identity to SEQ ID NO:33, SEQ ID NO:34, and SEQ ID NO:35; at least three target hybridizing sequences selected from the group consisting of sequences with at least 90% sequence identity to SEQ ID NO:36, SEQ ID NO:37, SEQ ID NO:38, and SEQ ID NO:39; at least three target hybridizing sequences selected from the group consisting of sequences with at least 90% sequence identity to SEQ ID NO:40, SEQ ID NO:41, SEQ ID NO:42, and SEQ ID NO:43; at least three target hybridizing sequences selected from the group consisting of sequences with at least 90% sequence identity to SEQ ID NO:44, SEQ ID NO:45, and SEQ ID NO:46; or at least three target hybridizing sequences selected from the group consisting of sequences with at least 90% sequence identity to SEQ ID NO:47, SEQ ID NO:48, and SEQ ID NO:49.

In one embodiment, a multiplex comprises at least two amplification oligomers and probe combinations wherein the first amplification oligomers and probe combination comprises, consists, or consists essentially of at least three target hybridizing sequence selected from the group consisting of sequences with at least 90% sequence identity to SEQ ID NO:27, SEQ ID NO:28, and SEQ ID NO:29 and wherein the second amplification oligomers and probe combination comprises, consists, or consists essentially of: at least three target hybridizing sequences selected from the group consisting of sequences with at least 90% sequence identity to SEQ ID NO:27, SEQ ID NO:28, and SEQ ID NO:29; at least three target hybridizing sequences selected from the group consisting of sequences with at least 90% sequence identity to SEQ ID NO:33, SEQ ID NO:34, and SEQ ID NO:35; at least three target hybridizing sequences selected from the group consisting of sequences with at least 90% sequence identity to SEQ ID NO:36, SEQ ID NO:37, SEQ ID NO:38, and SEQ ID NO:39; at least three target hybridizing sequences selected from the group consisting of sequences with at least 90% sequence identity to SEQ ID NO:40, SEQ ID NO:41, SEQ ID NO:42, and SEQ ID NO:43; at least three target hybridizing sequences selected from the group consisting of sequences with at least 90% sequence identity to SEQ ID NO:44, SEQ ID NO:45, and SEQ ID NO:46; or at least three target hybridizing sequences selected from the group consisting of sequences with at least 90% sequence identity to SEQ ID NO:47, SEQ ID NO:48, and SEQ ID NO:49.

In one embodiment, a multiplex comprises at least two amplification oligomers and probe combinations wherein the first amplification oligomers and probe combination comprises, consists, or consists essentially of at least three target hybridizing sequence selected from the group consisting of sequences with at least 90% sequence identity to SEQ ID NO:27, SEQ ID NO:28, and SEQ ID NO:29 and wherein the second amplification oligomers and probe combination comprises, consists, or consists essentially of: at least three target hybridizing sequences selected from the group consisting of sequences with at least 90% sequence identity to SEQ ID NO:30, SEQ ID NO:31, and SEQ ID NO:32; at least three target hybridizing sequences selected from the group consisting of sequences with at least 90% sequence identity to SEQ ID NO:33, SEQ ID NO:34, and SEQ ID NO:35; at least three target hybridizing sequences selected from the group consisting of sequences with at least 90% sequence identity to SEQ ID NO:36, SEQ ID NO:37, SEQ ID NO:38, and SEQ ID NO:39; at least three target hybridizing sequences selected from the group consisting of sequences with at least 90% sequence identity to SEQ ID NO:40, SEQ ID NO:41, SEQ ID NO:42, and SEQ ID NO:43; at least three target hybridizing sequences selected from the group consisting of sequences with at least 90% sequence identity to SEQ ID NO:44, SEQ ID NO:45, and SEQ ID NO:46; or at least three target hybridizing sequences selected from the group consisting of sequences with at least 90% sequence identity to SEQ ID NO:47, SEQ ID NO:48, and SEQ ID NO:49.

In one embodiment, a multiplex comprises at least two amplification oligomers and probe combinations wherein the first amplification oligomers and probe combination comprises, consists, or consists essentially of at least three target hybridizing sequence selected from the group consisting of sequences with at least 90% sequence identity to SEQ ID NO:33, SEQ ID NO:34, and SEQ ID NO:35 and wherein the second amplification oligomers and probe combination comprises, consists, or consists essentially of: at least three target hybridizing sequences selected from the group consisting of sequences with at least 90% sequence identity to SEQ ID NO:36, SEQ ID NO:37, SEQ ID NO:38, and SEQ ID NO:39; at least three target hybridizing sequences selected from the group consisting of sequences with at least 90% sequence identity to SEQ ID NO:40, SEQ ID NO:41, SEQ ID NO:42, and SEQ ID NO:43; at least three target hybridizing sequences selected from the group consisting of sequences with at least 90% sequence identity to SEQ ID NO:44, SEQ ID NO:45, and SEQ ID NO:46; or at least three target hybridizing sequences selected from the group consisting of sequences with at least 90% sequence identity to SEQ ID NO:47, SEQ ID NO:48, and SEQ ID NO:49.

In one embodiment, a multiplex comprises at least two amplification oligomers and probe combinations wherein the first amplification oligomers and probe combination comprises, consists, or consists essentially of at least three target hybridizing sequence selected from the group consisting of sequences with at least 90% sequence identity to SEQ ID NO:36, SEQ ID NO:37, SEQ ID NO:38, and SEQ ID NO:39 and wherein the second amplification oligomers and probe combination comprises, consists, or consists essentially of: at least three target hybridizing sequences selected from the group consisting of sequences with at least 90% sequence identity to SEQ ID NO:40, SEQ ID NO:41, SEQ ID NO:42, and SEQ ID NO:43; at least three target hybridizing sequences selected from the group consisting of sequences with at least 90% sequence identity to SEQ ID NO:44, SEQ ID NO:45, and SEQ ID NO:46; or at least three target hybridizing sequences selected from the group consisting of sequences with at least 90% sequence identity to SEQ ID NO:47, SEQ ID NO:48, and SEQ ID NO:49.

In one embodiment, a multiplex comprises at least two amplification oligomers and probe combinations wherein the first amplification oligomers and probe combination comprises, consists, or consists essentially of at least three target hybridizing sequence selected from the group consisting of sequences with at least 90% sequence identity to SEQ ID NO:40, SEQ ID NO:41, SEQ ID NO:42, and SEQ ID NO:43 and wherein the second amplification oligomers and probe combination comprises, consists, or consists essentially of: at least three target hybridizing sequences selected from the group consisting of sequences with at least 90% sequence identity to SEQ ID NO:44, SEQ ID NO:45, and SEQ ID NO:46; or at least three target hybridizing sequences selected from the group consisting of sequences with at least 90% sequence identity to SEQ ID NO:47, SEQ ID NO:48, and SEQ ID NO:49.

In one embodiment, a multiplex comprises at least two amplification oligomers and probe combinations wherein the first amplification oligomers and probe combination comprises, consists, or consists essentially of at least three target hybridizing sequence selected from the group consisting of sequences with at least 90% sequence identity to SEQ ID NO:44, SEQ ID NO:45, and SEQ ID NO:46 and wherein the second amplification oligomers and probe combination comprises, consists, or consists essentially of at least three target hybridizing sequences selected from the group consisting of sequences with at least 90% sequence identity to SEQ ID NO:4, SEQ ID NO:48, and SEQ ID NO:49.

In another embodiment, a multiplex comprising at least two amplification oligomers and probe combinations further includes a third amplification oligomers and probe combination comprising internal control (IC) amplification primers and probe. In one embodiment, the third amplification oligomer and probe set comprises, consists, or consists essentially of: at least three target hybridizing sequences selected from the group consisting of sequences with at least 90% sequence identity to SEQ ID NO:50, SEQ ID NO:51, and SEQ ID NO:52; or at least three target hybridizing sequences selected from the group consisting of sequences with at least 90% sequence identity to SEQ ID NO:53, SEQ ID NO:54, and SEQ ID NO:55.

The oligomers for use in the methods described herein are suited for preparation of kits. Such a kit may comprise containers, each with one or more of the various oligomers optionally together with one or more of the reagents or enzymes required to perform the methods described herein. The components of the kit may be supplied in concentrated form. A set of instructions for using the components of the kit will also typically be included. Where the kit comprises combinations of oligomers then the individual oligomers may be provided in individual form, with appropriate instructions for mixing same, or combinations thereof that are ready mixed.

The detection of an amplicon from a sample using primers of the instant invention is indicative of the presence of a Shiga toxin gene in the sample. The detection of an amplicon from a sample using primers and probes of the instant invention is indicative of the presence of STEC in the sample. The detection of amplified target sequences characteristic of a Shiga toxin gene in a biological sample from an individual is indicative of infection with a bacterium containing a Shiga toxin. The detection of an amplicon in a human biological sample using the primer pairs described herein is indicative of an infection of the human with a bacterium containing a Shiga toxin. The detection of an amplicon in a human biological sample using the primer and probe combinations described herein is also indicative of such an infection in that human.

EXAMPLES

Example 1

Exemplary Nucleic Acid Sequences

This example provides exemplary sequences that are useful with the present invention. Table 2 does not limit the scope of the invention. Sequences are presented according to Tables 1 through 6 of Appendix 2 of the World Intellectual Property Organization (WIPO) Handbook on Industrial Property Information and Documentation, Standard ST.25 (1998). The sequences in Table 2 are associated with sequence identifiers (SEQ ID NOs) and the function of each sequence (forward primer, reverse primer or probe) is also indicated as well as the target.

TABLE 2

Exemplary nucleic acid sequences

| SEQ ID NO: | Sequence 5'→3' | Function | Target |
|---|---|---|---|
| 1 | TGACAGTAGCTATACCACGT | Forward primer | stx1 |
| 2 | AGTGTTGTACGAAATCCCCT | Reverse primer | stx1 |

TABLE 2 -continued

Exemplary nucleic acid sequences

| SEQ ID NO: | Sequence 5'→3' | Function | Target |
|---|---|---|---|
| 3 | ATCAGTCGTACGGGGATGCAGA | Probe | stx1 |
| 4 | ACAGCGTGTTGCAGGGATCAGTC | Probe | stx1 |
| 5 | ATGCAGATAAATCGCCATTCGTTGAC | Probe | stx1 |
| 6 | CTATGCGACATTAAATCCAGAT | Reverse primer | stx1 |
| 7 | TAGTCAACGAATGGCGATTTATCTGCA | Probe | stx1 |
| 8 | AGACGTATGTAGATTCGCTG | Forward primer | stx1 |
| 9 | TGGATCTATCCCTCTGACAT | Reverse primer | stx1 |
| 10 | ATGTCATTCGCTCTGCAATAGGTACT | Probe | stx1 |
| 11 | ATCATCAGTAAAGACGTACCTCCTGAT | Probe | stx1 |
| 12 | GCTGATTTTTCACATGTTACCT | Forward primer | stx1 |
| 13 | CTATGCGACATTAAATCCAGAT | Reverse primer | stx1 |
| 14 | TTGTCTGGTGACAGTAGCTATACCAC | Probe | stx1 |
| 15 | AGGGGATTTCGTACAACACT | Forward primer | stx1 |
| 16 | AATTCAGTATTAATGCCACGCT | Reverse primer | stx1 |
| 17 | ACACGAACAGAGTCTTGTCCATGATA | Probe | stx1 |
| 18 | ATGATCTCAGTGGGCGTTCTTATGTA | Probe | stx1 |
| 19 | AGAGCGATGTTACGGTTTGT | Forward primer | stx1 |
| 20 | ATCAACATCTTCAGCAGTCATT | Reverse primer | stx1 |
| 21 | AGCTGAAGCTTTACGTTTTCGGCAAAT | Probe | stx1 |
| 22 | CATAAGAACGCCCACTGAGATCATC | Probe | stx1 |
| 23 | GAAGCTTTACGTTTTCGGCA | Forward primer | stx1 |
| 24 | GAACAGAGTCTTGTCCATGA | Reverse primer | stx1 |
| 25 | CTACTCAACCTTCCCCAGTTCAATG | Probe | stx1 |
| 26 | AGAGGGGATTTCGTACAACACTGGA | Probe | stx1 |
| 27 | GTGGCATTAATACTGAATTGTC | Forward primer | stx1 |
| 28 | ACAATATTTTATTGTGCGTAATCC | Reverse primer | stx1 |
| 29 | ATCATGCATCGCGAGTTGCCAGAA | Probe | stx1 |
| 30 | CGATACCTTTACAGTTAAAGTG | Forward primer | stx1 |
| 31 | TCCATTATGACAGGCATTAGTT | Reverse primer | stx1 |
| 32 | ATGGAATCTTCAGTCTCTTCTTCTCAGT | Probe | stx1 |
| 33 | GGGTACTGTGCCTGTTAC | Forward primer | stx2 |
| 34 | GTCCGTATACTATTTAACGAAG | Reverse primer | stx2 |
| 35 | TTCTTCGGTATCCTATTCCCGGGA | Probe | stx2 |
| 36 | CATGACAACGGACAGCAG | Forward primer | stx2 |
| 37 | CTCCATTAACGCCAGATATG | Reverse primer | stx2 |
| 38 | ACCAGTGAGTGACGACTGATTTGCAT | Probe | stx2 |
| 39 | ATACCACTCTGCAACGTGTCGCA | Probe | stx2 |
| 40 | CAGAGATGCATCCAGAGC | Forward primer | stx2 |

TABLE 2 -continued

Exemplary nucleic acid sequences

| SEQ ID NO: | Sequence 5'→3' | Function | Target |
|---|---|---|---|
| 41 | CCGGAAGCACATTGCTGA | Reverse primer | stx2 |
| 42 | CAGAGAGAATTTCGTCAGGCACTG | Probe | stx2 |
| 43 | ACAGGAGCAGTTTCAGACAGTGC | Probe | stx2 |
| 44 | GGACCTCACTCTGAACTG | Forward primer | stx2 |
| 45 | TATTATTAAAGGATATTCTCCCCA | Reverse primer | stx2 |
| 46 | TCAGCAATGTGCTTCCGGAGTATC | Probe | stx2 |
| 47 | GAATGTCAGATAAGTGGCGA | Forward primer | stx2 |
| 48 | CCGCCATTGCATTAACAGAA | Reverse primer | stx2 |
| 49 | TGCAAATAAAACCGCCATAAACATCTTCT | Probe | stx2 |
| 50 | CAGGAGCGTAGGAATACCATC | Forward primer | Internal control |
| 51 | GGGCTAACTGTGAAGATTCAATAG | Reverse primer | Internal control |
| 52 | TCACTGATTCAAGCACGTTAGAAGGCCA | Probe | Internal control |
| 53 | GAGTTGGTAAACAGATCATGC | Forward primer | Internal control |
| 54 | GACTTGTGGCCTTCTAACG | Reverse primer | Internal control |
| 55 | TATCGAGCACAGGAGCGTAGGAATA | Probe | Internal control |

SEQ ID NOs: 56 and 57 (below) are the sequences of stx1 and stx2, respectively, of a strain of *E. coli* O157:H7.

```
Escherichia coli O157:H7 str. Sakai DNA, complete genome GenBank
accession number BA000007, GI number 47118301 bases 2924490-2925719
                                                            SEQ ID NO: 56
aatatgaaaataattatttttagagtgctaacttttttctttgttatcttttcagttaatgtggttgcgaaggaa tttaccttagacttctcgactgcaaagacgtatgtagattcgctgaatgtcattcgctctgcaataggtactcca ttacagactatttcatcaggaggtacgtctttactgatgattgatagtggcacaggggataatttgtttgcagtt gatgtcagagggatagatccagaggaagggcggtttaataatctacggcttattgttgaacgaaataatttatat gtgacaggatttgttaacaggacaaataatgttttttatcgctttgctgattttttcacatgttacctttccaggt acaacagcggttacattgtctggtgacagtagctataccacgttacagcgtgttgcagggatcagtcgtacgggg atgcagataaatcgccattcgttgactacttcttatctggatttaatgtcgcatagtggaacctcactgacgcag tctgtggcaagagcgatgttacggtttgttactgtgacagctgaagctttacgttttcggcaaatacagagggga tttcgtacaacactggatgatctcagtgggcgttcttatgtaatgactgctgaagatgttgatcttacattgaac tggggaaggttgagtagtgtcctgcctgattatcatggacaagactctgttcgtgtaggaagaatttcttttgga agcattaatgcaattctgggaagcgtggcattaatactgaattgtcatcatcatgcatcgcgagttgccagaatg gcatctgatgagtttccttctatgtgtccggcagatggaagagtccgtgggattacgcacaataaaatattgtgg gattcatccactctgggggcaattctgatgcgcagaactattagcagttgaggggtaaaatgaaaaaacatta ttaatagctgcatcgctttcatttttttcagcaagtgcgctggcgacgcctgattgtgtaactggaaaggtggag tatacaaaatataatgatgacgatacctttacagttaaagtgggtgataaagaattatttaccaacagatggaat cttcagtctcttcttctcagtgcgcaaattacggggatgactgtaaccattaaaactaatgcctgtcataatgga gggggattcagcgaagttattttttcgttga,
```

-continued

Escherichia coli O157:H7 str. Sakai DNA, complete genome GenBank
accession number BA000007, GI number 47118301 bases 1266965-1268205

SEQ ID NO: 57 atgaagtgtatattatttaaatgggtactgtgcctgttactgggttttcttcggtatcctattcccgggagttt acgatagacttttcgacccaacaaagttatgtctcttcgttaaatagtatacggacagagatatcgacccctctt gaacatatatctcaggggaccacatcggtgtctgttattaaccacacccaccgggcagttattttgctgtggat atacgagggcttgatgtctatcaggcgcgttttgaccatcttcgtctgattattgagcaaaataatttatatgtg gccgggttcgttaatacggcaacaaatactttctaccgttttcagattttacacatatatcagtgcccggtgtg acaacggtttccatgacaacggacagcagttataccactctgcaacgtgtcgcagcgctggaacgttccggaatg caaatcagtcgtcactcactggtttcatcatatctggcgttaatggagttcagtggtaatacaatgaccagagat gcatccagagcagttctgcgttttgtcactgtcacagcagaagccttacgcttcaggcagatacagagagaattt cgtcaggcactgtctgaaactgctcctgtgtatacgatgacgccgggagacgtggacctcactctgaactggggg cgaatcagcaatgtgcttccggagtatcggggagaggatggtgtcagagtggggagaatatcctttaataatata tcagcgatactggggactgtggccgttatactgaattgccatcatcaggggcgcgttctgttcgcgccgtgaat gaagagagtcaaccagaatgtcagataactggcgacaggcctgttataaaaataaacaatacattatgggaaagt aatacagctgcagcgtttctgaacagaaagtcacagttttatatacaacgggtaaataaaggagttaagcatga agaagatgtttatggcggttttatttgcattagcttctgttaatgcaatggcggcggattgtgctaaaggtaaaa ttgagttttccaagtataatgaggatgacacatttacagtgaaggttgacgggaaagaatactggaccagtcgct ggaatctgcaaccgttactgcaaagtgctcagttgacaggaatgactgtcacaatcaaatccagtacctgtgaat caggctccggatttgctgaagtgcagtttaataatgactga, Example 2

Preparation of DNA

All strains of STEC, including various (O157 and non-O157 strains) were obtained from the STEC Center at Michigan State University). All bacteria were cultured by streaking onto agar plates, incubating overnight at 37° C., and transferring to 4° C. the next morning. Individual colonies were selected, inoculated into 3 mL of Luria broth, incubated overnight at 37° C., and transferred to 4° C. the next morning. A 20 µL aliquot of the inoculated broth was serially diluted (dilution range was 10-$10^{10}$) to determine colony counts. A volume of 100 µL of each serial dilution was spread on an agar plate, incubated overnight at 37° C., and the colonies were counted the next day. DNA was isolated from the bacteria using two different methods. The first method used the NucliSENS® easyMag® and associated reagents available and sold by bioMérieux (Durham, N.C.). In the second method, the bacteria were placed in Cary-Blair medium with 0.1 mm glass beads and vortexed for 10 minutes with the tube lying horizontally.

Example 3

Initial Testing of Shiga Toxin Gene 1 and Shiga Toxin Gene 2 Primers

In this example, primers specific for the Shiga toxin gene 1 (stx1) and Shiga toxin gene 2 (stx2) were evaluated to determine if they would amplify the target gene and not amplify non-target genes. The primers were evaluated using the following bacteria: Shiga Toxin producing *E. coli* (STEC), *Shigella flexneri*, *Salmonella enterica* sv. Typhimurium, *Campylobacter jejuni*, *Shigella sonnei*, and *Salmonella enterica* sv. Enteritidis. The primer combinations, along with the expected size in base pairs (bp), are shown in Table 3, below. Combination numbers P1-P9 target stx1 and combination numbers P10-P14 target stx2.

TABLE 3

Amplification Primer Pair Combinations

| Primer Pair Combination No. | Forward SEQ ID NO: | Reverse SEQ ID NO: | Expected Amplicon Size (bp) |
|---|---|---|---|
| P1 | 1 | 2 | 217 |
| P2 | 1 | 6 | 108 |
| P3 | 8 | 9 | 146 |
| P4 | 12 | 13 | 162 |
| P5 | 15 | 16 | 200 |
| P6 | 19 | 20 | 129 |
| P7 | 23 | 24 | 161 |
| P8 | 27 | 28 | 124 |
| P9 | 30 | 31 | 130 |
| P10 | 33 | 34 | 109 |
| P11 | 36 | 37 | 115 |
| P12 | 40 | 41 | 181 |
| P13 | 44 | 45 | 95 |
| P14 | 47 | 48 | 191 |

The primers were evaluated at a concentration of 250 µM, using various concentrations of bacteria. Five µL volumes of solutions containing bacteria at various concentrations or dilutions were added to amplification mixtures. Bacterial targets other than *Salmonella Enteritidis* and *Shigella sonnei* were diluted to provide 1, 10, $10^2$, $10^3$, $10^5$ copies of bacterial DNA per µL in 5 µL. *Salmonella Enteritidis* and Shigella sonnei were provided as 54 of bacterial stocks. The amplification mixtures were subjected to amplification by PCR using an ABI 2720 thermocycler with the following conditions: 1 cycle of 95° C. for 10 minutes; 50 cycles of 95° C. for 15 seconds and 55° C. for 35 seconds. The amplification product was detected by capillary electrophoresis using Qiagen QIAxcel cartridges. The results of this experiment are outlined in Table 4 below. The comment field provides notes regarding interpretation of the results. It was later determined that the *Shigella flexneri* genomic DNA was contaminated with STEC genomic DNA and therefore, a cross-reaction with *Shigella flexneri* as template resulting in the expected amplicon size for a stx gene target in Table 4 does not represent an adverse result. On the basis of these results, primer pair combination P3 (SEQ ID NOs: 8 and 9) targeting the stx1 gene and primer pair combination P11 (SEQ ID NOs: 36 and 37) targeting stx2 gene, were among the primer pairs selected for further testing.

combination number. PPC1 to PPC5 target the stx1 gene and PPC6 to PPC8 target the stx2 gene.

TABLE 5

| Bacteria Tested | |
|---|---|
| Bacteria | ATCC No. |
| *Salmonella enterica* sv *Typhi* | 6539 |
| *Salmonella enterica* sv *Newport* | 6962 |
| *Salmonella enterica* sv *Heidelberg* | 8326 |
| *Salmonella enterica* sv *Typhimurium* | 14028 |
| *Salmonella bongori* | 43975 |
| *Salmonella enterica* sv *Typhimurium* | BAA-189 |
| *Salmonella enterica* sv *Paratyphi* B | 8759 |
| *Salmonella enterica* sv *Typhimurium* | BAA-191 |
| *Salmonella enterica* sv *Newport* | 27869 |
| *Salmonella enterica* sv *Enteritidis* | 6961 |
| *Salmonella enterica* sv *Typhimurium* | BAA-215 |
| *Salmonella enterica* sv *Enteritidis* | 4931 |
| *Salmonella enterica* sv *Typhimurium* | 19585 |

TABLE 4

Detection of *E. coli* Amplification Products

| Primer Pair Combination | Expected Amplicon Size (bp) | Lowest Concentration of *E. coli* Detected (copies/µL) | Comments |
|---|---|---|---|
| P1 | 217 | 4.75 | Detected an *E. coli* band at 189 bp & an *S. sonnei* band at 644 bp |
| P2 | 108 | 5.23 | Detected a ~85 bp band for *Salmonella* species |
| P3 | 146 | 8.2 | cross-reaction with *Shigella flexneri* at 151 bp (7.18 ng/µL) |
| P4 | 162 | 8.5 | |
| P5 | 200 | 7.79 | cross-reaction with *Shigella flexneri* evidenced by band at 195 bp (6.18 ng/µL) and primer dimer (~50 bp) for *C. coli, S. sonnei* |
| P6 | 129 | 8.34 | Detected an *S. sonnei* band at 669 bp |
| P7 | 161 | 996 | Poor sensitivity |
| P8 | 124 | 1.94 | |
| P9 | 130 | 5.08 | *E. coli* band detected at 122 bp |
| P10 | 109 | 4.79 | |
| P11 | 115 | 7.49 | Cross-reaction with *Shigella flexneri* (e.g., band at 115 bp (5.25 ng/µL)) was later determined to be STEC genomic DNA contamination of the *Shigella flexneri* stock. Primer dimers were observed (~48 bps) in all samples except the negative control. *S. enterica* also detected with bands at 387 bp and 474 bp. |
| P12 | 181 | 7.34 | *S. enterica* detected with bands at 419 bp and 528 bp. *S. flexneri* detected with band at 287 bp. *S. sonnei* detected with bands at 129 and 326 bp (6.74 ng/µL). The negative control has a band at 80 bp band. |
| P13 | 95 | 4.18 | *S. typhimurium* 44 bp band (primer dimer) |
| P14 | 191 | 929 | Poor sensitivity |

Example 4

Specificity Testing of Select Shiga Toxin Gene 1 and Shiga Toxin Gene 2 Primers and Probes In this example, primers and probes targeting the Shiga toxin gene 1 (stx1) and Shiga toxin gene 2 (stx2) were evaluated for cross-reactivity to the bacteria listed in Table 5, below. The primer and probe combinations are shown in Table 6, below, where "PPC #" indicates the primer/probe TABLE 5-continued

| Bacteria Tested | |
|---|---|
| Bacteria | ATCC No. |
| *Salmonella enterica* sv *Enteritidis* | BAA-708 |
| *Salmonella enterica* sv *Enteritidis* | BAA-1045 |
| *Salmonella enterica* sv *Montevideo* | BAA-710 |
| *Salmonella enterica* subspecies | BAA-1593 |

TABLE 5-continued

Bacteria Tested

| Bacteria | ATCC No. |
| --- | --- |
| enterica sv Javiana | |
| Salmonella enterica subspecies enterica sv Typhimiurium | BAA-1603 |
| Shigella sonnei | 9290 |
| Shigella flexneri | 12022 |
| Shigella sonnei | 29930 |
| Shigella sonnei | 11060 |
| Shigella flexneri serotype 6 | 12025 |
| Shigella dysenteriae | 29027 |
| Shigella sonnei | 25931 |
| Shigella dysenteriae | 29026 |
| Shigella boydii serotype 2 | 25930 |
| Shigella flexneri serotype 3 | 11836 |
| Shigella boydii serotype 1 | 9207 |
| Shigella flexneri serotype 2a | 25875 |
| Shigella sonnei | 29030 |
| Shigella flexneri serotype 1a | 9199 |
| Campylobacter jejuni ssp. jejuni | 22428 |
| Campylobacter fetus ssp. fetus | 33246 |
| Campylobacter jejuni ssp. jejuni | 3329 |
| Campylobacter coli | 43474 |

TABLE 6

Primer and Probe Combinations

| Primer Pair-Probe Combination No. | Forward SEQ ID NO: | Reverse SEQ ID NO: | Probe SEQ ID NO: |
| --- | --- | --- | --- |
| PPC1 | 1 | 2 | 5 |
| PPC2 | 8 | 9 | 10 |
| PPC3 | 8 | 9 | 11 |
| PPC4 | 19 | 20 | 21 |
| PPC5 | 23 | 24 | 25 |
| PPC6 | 33 | 34 | 35 |
| PPC7 | 36 | 37 | 38 |
| PPC8 | 36 | 37 | 39 |

The primers and probes were evaluated at 200 μM, using various concentrations of bacteria. The probes for primer/probe combinations PPC1 to PPC5 were labeled with CalOrange and BHQ1 (BioSearch Technologies, Novato, Calif.). The probes for primer/probe combinations PPC6 to PPC8 were labeled with FAM and BHQ1 (BioSearch Technologies, Novato, Calif.). Nucleic acids were extracted from 5 μL solutions containing bacteria at either $10^5$ CFU/mL or $10^{-4}$ dilution of ATCC stock solutions by providing 200 μL of dilution to an easyMAG system (BioMerieux, Durham, N.C., Nucleisens EasyMAG), and eluting into 110 μL volume. Eluted nucleic acids were amplified by PCR on a Cepheid SmartCycler® (Sunnyvale, Calif.), using the following protocol: 1 cycle of 95° C. for 10 minutes; 5 cycles of 95° C. for 30 seconds and 55° C. for 60 seconds; and 45 cycles of 95° C. for 10 seconds and 55° C. for 60 seconds. The positive control was E. coli strain EDL 933 genomic DNA, (Item #700927D, Lot #3791888, $1 \times 10^5$ copies/μL diluted 1:10 before use. Water was used as a negative control. The controls verified that the assay operates as intended. All of the stx1 primer/probe combinations were found to cross-react with Shigella dysenteriae, ATCC #29026. This was an expected result because this strain contains a Shiga Toxin gene similar to stx1. On the other hand, none of the stx2 primer/probe combinations were found to cross-react with any of the bacteria. Primer/probe combination PPC5 had false positives with the positive control. This is due to "bleed-over" of the detection label into alternative detection channels and is based on the optics of the system. There was also some erroneous optics in primer/probe combinations 1-5, but only with the S. dysenteriae where it would test positive in the CalOrange (TET) channel generating erroneous curves in the FAM channel due to the high signal generated in the TET channel. The results of this example indicate that the primer-probe combinations targeted to stx1 can be used to identify a specific strain of Shigella dysenteriae (29026) which is known to contain a Shiga toxin. It was not previously known whether this strain carries the stx1 gene or the stx2 gene and it now appears that this strain carries the stx1-like gene. This experiment also demonstrates proper functioning of the selected probes with the primer pairs.

Example 5

Specificity and Reliability of Shiga Toxin 1, Shiga Toxin 2, and Internal Control Triplex Primer-Probe Combinations In this example, seven primer and probe combinations for Shiga toxin gene 1 (stx1) and Shiga toxin gene 2 (stx2) were evaluated in a triplex reaction with an internal control primer and probe combination. Twenty-one strains of E. coli were evaluated. The 21 strains are EcMLST numbers TW14960, TW02302, TW07927, TW07814, TW09153, TW08569, TW07926, TW00975, TW07960, TW04863, TW05149, TW07596, TW07989, TW07591, TW07700, TW07931, TW07947, TW08101, TW06296, TW00971, and TW09183. Each EcMLST number represents a strain of pathogenic E. coli characterized by multi-locus sequence typing. The EcMLST database can be accessed via the internet or by contacting Microbial Evolution Laboratory, 165 National Food Safety and Toxicology Center, Michigan State University, East Lansing, Mich. 48824. The other bacteria investigated include Salmonella bongori, Salmonella enterica subsp enterica ser Typhi, Salmonella enterica subsp enterica ser Paratyphi, Salmonella enterica subsp enterica ser Typhimurium (6 strains), Salmonella enterica subsp enterica ser Enteritidis (4 strains), Salmonella enterica subsp enterica ser Newport (2 strains), Salmonella enterica subsp enterica ser Heidelberg, Salmonella enterica subsp enterica ser Javiana, Salmonella enterica subsp enterica ser Montevideo, Shigella boydii (2 strains), Shigella dysenteriae (2 strains), Shigella flexneri (5 strains), Shigella sonnei (6 strains), Campylobacter jejuni subsp jejuni (7 strains), Campylobacter coli (4 strains), Campylobacter lari (2 strains), Campylobacter upsaliensis (2 strains), Campylobacter hyointestinalis, Campylobacter fetus sub fetus, Campylobacter helveticus, Campylobacter gracilis, Campylobacter curvus, Campylobacter sputorum biovar sputorum, Campylobacter sputorum biovar faecalis, Campylobacter rectus, Campylobacter showae, and Campylobacter mucosalis. The primer and probe combinations tested are shown in Table 7, below. "PPC #" indicates the primer/probe combination number with reference to the codes shown in Table 6 above (PPC1 to PPC8). PPC9 has a forward primer of SEQ ID NO: 19, a reverse primer of SEQ ID NO: 20, and a probe of SEQ ID NO: 22.

TABLE 7

Primer and Probe Combinations

| MIXTURE# | stx1 Primer Probe Set | stx2 Primer Probe Set |
|---|---|---|
| M1 | PPC1 | PPC7 |
| M2 | PPC2 | PPC7 |
| M3 | PPC2 | PPC8 |
| M4 | PPC3 | PPC7 |
| M5 | PPC3 | PPC8 |
| M6 | PPC9 | PPC7 |
| M7 | PPC9 | PPC8 |

Each primer and probe was evaluated at 200 μM. The probes for stx1 were labeled with CALflour0560 and BHQ1, the probes for stx2 were labeled with FAM and BHQ1, and the probes for the IC were labeled with Quasar670 and BHQ2. Primer/probe combinations were evaluated using $10^4$ CFU/μL and $10^3$ CFU/μl of extracted *E. coli* nucleic acids and all other bacteria were extracted and their resultant nucleic acids tested at various concentrations. Each reaction mixture also contained a primer pair for amplification of an internal control polynucleotide and a probe. This primer and probe set is used as an internal control to verify if any PCR inhibitors are present in the sample and determine that PCR amplification conditions are operating properly. A 5 μL volume of each nucleic acid extract of bacteria was amplified using PCR using the Cepheid SmartCycler® system with the following protocol: 1 cycle of 95° C. for 60 seconds; 5 cycles of 95° C. for 30 seconds and 55° C. for 60 seconds; and 45 cycles of 95° C. for 10 seconds and 55° C. for 60 seconds. No detections were observed for any of the strains that do not contain the stx1 or stx2 genes. Shown below in Table 8 are the cycle threshold (Ct) values (wherein lower numbers indicate more efficient amplification) for the 12 strains containing the stx2 gene in PCR reactions. Table entries with "0" indicate an amplification failure. In these cases, the average Ct values are calculated accordingly, with the "0" entries are omitted from the calculation. It can be seen that the mean Ct is the lowest for mixture M5 which contains primer probe combinations PPC3 (SEQ ID NOs: 8, 9 and 11) and PPC8 (SEQ ID Nos: 36, 37 and 39). It is also seen that mixture M5 did not have any amplification failures. This example provides an indication that mixture M5 is efficient for amplification with respect to stx2. Additional experiments (not shown) have confirmed that mixture M5 is also effective for amplification of stx1.

TABLE 8

Cycle Threshold Values Determined for Dual Target Mixtures in Amplification Reactions with Samples Containing stx2

| Sample ID | M1 | M2 | M3 | M4 | M5 | M6 | M7 |
|---|---|---|---|---|---|---|---|
| 1 at 10^4 CFU/mL | 33 | 33.3 | 33.4 | 33.2 | 33 | 33.5 | 33 |
| 1 at 10^3 CFU/mL | 36 | 36.8 | 36.4 | 39.2 | 35.7 | 38.1 | 36.6 |
| 2 at 10^4 CFU/mL | 32.3 | 32.3 | 32.1 | 32.1 | 32.2 | 32.9 | 32.3 |
| 2 at 10^3 CFU/mL | 34.9 | 35.1 | 37.8 | 35.7 | 35.3 | 36.5 | 35.7 |
| 3 at 10^4 CFU/mL | 33.7 | 33.3 | 33.4 | 34.1 | 33.1 | 33.6 | 33.3 |
| 3 at 10^3 CFU/mL | 35.7 | 0 | 37.2 | 37.3 | 35.7 | 36.4 | 37.6 |
| 4 at 10^4 CFU/mL | 32.2 | 32 | 32.2 | 32.4 | 33.1 | 32.2 | 32.1 |
| 4 at 10^3 CFU/mL | 35.1 | 35.3 | 35 | 35.6 | 34.7 | 35.2 | 35.4 |
| 5 at 10^4 CFU/mL | 32.3 | 32.9 | 33.3 | 32.2 | 32.2 | 32.8 | 32.7 |
| 5 at 10^3 CFU/mL | 36.1 | 38.6 | 35.8 | 37.9 | 34.9 | 35.5 | 36.5 |
| 6 at 10^4 CFU/mL | 32.7 | 32.7 | 33.5 | 32.5 | 32.4 | 32.9 | 32.9 |
| 6 at 10^3 CFU/mL | 36.2 | 36.8 | 35.5 | 35.1 | 35 | 35.6 | 36.3 |
| 7 at 10^4 CFU/mL | 32.2 | 33.5 | 33.4 | 32.4 | 31.9 | 33.4 | 32.4 |
| 7 at 10^3 CFU/mL | 36.2 | 36.2 | 0 | 38.4 | 35.8 | 0 | 0 |
| 8 at 10^4 CFU/mL | 31.2 | 31.8 | 31.6 | 31.4 | 31.7 | 32.5 | 31.4 |
| 8 at 10^3 CFU/mL | 34.3 | 34.8 | 34.5 | 34.6 | 35.1 | 34.7 | 34.3 |
| 9 at 10^4 CFU/mL | 30.3 | 31 | 31.8 | 31.1 | 30.7 | 31.3 | 31.2 |
| 9 at 10^3 CFU/mL | 33.6 | 34.1 | 33.7 | 34.2 | 34.3 | 33.4 | 34.5 |
| 10 at 10^4 CFU/mL | 32.1 | 32.4 | 32.7 | 32.3 | 32 | 33.1 | 31.9 |
| 10 at 10^3 CFU/mL | 35.5 | 36.5 | 39.1 | 35.7 | 36.5 | 35.7 | 38.2 |
| 11 at 10^4 CFU/mL | 33.1 | 33.2 | 33.6 | 33.3 | 32.4 | 33.4 | 33.3 |
| 11 at 10^3 CFU/mL | 37.1 | 35.4 | 37.2 | 36.1 | 36.2 | 36.5 | 36.7 |
| 12 at 10^4 CFU/mL | 31.5 | 31.1 | 30.9 | 31.2 | 30.9 | 31.8 | 31.1 |
| 12 at 10^3 CFU/mL | 34.3 | 35.7 | 34.7 | 34.5 | 34.1 | 34.2 | 34.2 |
| Avg at 10^4 CFU/mL | 32.2 | 32.5 | 32.7 | 32.4 | 32 | 32.8 | 32.3 |
| Avg at 10^3 CFU/mL | 35.4 | 35.9 | 36.1 | 36.2 | 35.3 | 35.6 | 36 |
| Positive Control | 27.2 | 27.4 | 28 | 27.8 | 27.2 | 26.8 | 27.8 |

Results for stx1 and IC are not shown. It is notable that mixtures M2, M3, M4, M6, and M7 missed some detections at the lower of the two concentrations tested and/or had false positives for the stx1 detection. Mixture 1 had 3 instances of false positive results in the IC (CY5) channel exhibiting non-specific interaction of the oligonucleotides in that specific mix allowing for the Quasar 670 signal to be detected in the absence of any IC template. More specifically, mixture M2 missed a detection of stx2 at 10^3 CFU/mL of strain TW 07814. M3 missed a detection of stx1 at 10^3 CFU/mL in strain TW07960, missed detection of both stx1 and stx2 at 10^3 CFU/mL in strain TW4863, and had a false positive detection of stx1 in strain TW07931. Mixture M4 missed a detection of stx1 at 10^3 CFU/mL in strain TW04863, TW07947, and in strain TW08101 and had a false positive detection of stx1 in strain TW07927. Mixture M6 missed a detection of stx1 at 10^3 CFU/mL in strain TW07947 and missed a detection of stx2 at 10^3 in strain TW04863. These results indicate that mixtures M2, M3, M4, M6 and M7 are not as reliable as some of the other mixtures. Additional experiments (not shown) have also established that an internal control primer-probe set comprising SEQ ID NO:

53 (forward), SEQ ID NO: 54 (reverse), and SEQ ID NO: 55 (probe) works well with mixture M5. However, the skilled person will recognize that other internal control systems which include a template polynucleotide and a primer/probe set can be used to replace this internal control system. The skilled person will understand that such appropriate replacements of internal control systems can be identified without undue experimentation.

Example 6

Optimization of stx2/stx1 Primer-Probe Combinations

Based on data generated in, e.g., reactivity and limit of detection (LoD) studies in stool and clinical samples, three different stx2/stx1 primer-probe combinations (see Table 9, below) were selected for further evaluation and optimization using STEC genomic DNA as template.

TABLE 9 stx2/stx1 Primer-Probe Combinations

| Combination Designation (stx2/stx1) | SEQ ID NOS: | Name (Description) | 5' Modification | 3' Modification |
|---|---|---|---|---|
| 1a/9a | 33 | stx2 #1F (forward primer) | None | None |
|  | 34 | stx2 #1R (reverse primer) | None | None |
|  | 35 | stx2 #1a (Internal Quencher BHQ-1) (detection probe) | FAM | Spacer C3 |
|  | 30 | stx1 #9F (forward primer) | None | None |
|  | 31 | stx1 #9R (reverse primer) | None | None |
|  | 32 | stx1 #9a (detection probe) | CalO 560 | BHQ-1 |
| 3a/9a | 40 | stx2 #3F (forward primer) | None | None |
|  | 41 | stx2 #3R (reverse primer) | None | None |
|  | 42 | stx2 #3a (Internal Quencher BHQ-1) (detection probe) | FAM | Spacer C3 |
|  | 30 | stx1 #9F (forward primer) | None | None |
|  | 31 | stx1 #9R (reverse primer) | None | None |
|  | 32 | stx1 #9a (detection probe) | CalO 560 | BHQ-1 |
| 5a/6b | 47 | stx2 #5F (forward primer) | None | None |
|  | 48 | stx2 #5R (reverse primer) | None | None |
|  | 49 | stx2 #5a2 (Internal Quencher BHQ-1) (detection probe) | FAM | Spacer C3 |
|  | 19 | stx1 #6F (forward primer) | None | None |
|  | 20 | stx1 #6R (reverse primer) | None | None |
|  | 22 | stx1 #6b (detection probe) | CalO 560 | BHQ-1 |

An internal control (IC) primer and probe combination was included in the stx2/stx1 mixes. The IC forward and reverse primers (designated as DNA IC 4F (Adeno) and DNA IC 4R (Adeno), respectively) had the nucleotide base sequences of SEQ ID NO:53 and SEQ ID NO:54, respectively, without 5' or 3' modification. The IC detection probe (designated as DNA TM IC 4P) had the nucleotide base sequence of SEQ ID NO:55, labeled at its 5' end with Quasar 670 and at its 3' end with BHQ-2.

Materials utilized for real-time PCR included the following: 2× FastStart PCR Master (Roche); FastStart Taq 5u/µl (Roche); AccuGENE® Molecular Biology Water; STEC genomic DNA: *Escherichia coli* strain EDL 933 genomic DNA, ATCC Accession Nos. 700927D and 3791888, 7.8× $10^6$ c/µl stock.

Real-time PCR reactions were initially run with different stx2 primer concentrations. stx2 forward and reverse primers were run in separate reactions at 200 nM, 300 nM, and 400 nM final concentrations for each stx2/stx1 combination. stx1 and IC forward and reverse primers were each used at a final concentration of 250 nM, stx1 and stx2 probes were each used at a final concentration of 200 nM, and IC probe was used at a final concentration of 300 nM. Final FastStart PCR Master mix was 1×, and the final concentration of FastStart Taq was 4 units. Each mix was run with the STEC genomic DNA template at 10, 1, and 0.1 c/µL.

Each mix generated was frozen solid at −80° before use. For PCR, each DNA concentration and a no template control (water) were run in duplicate with a negative control in a single replicate with each mix. 20⊘ of the mix was added to individual Cepheid tubes and 5 µL of template added and mixed via pipetting. All Cepheid tubes were spun down in a mini-centrifuge prior to PCR on the Cepheid. The cycling parameters used on the Cepheid were 95° C. for 10 min (optics off), 5 cycles of 95° C. for 30 sec (optics off), 55° C. for 60 sec (optics on), 40 cycles of 95° C. for 10 sec (optics off), 55° C. for 60 sec (optics on).

The PCR runs for each mix were analyzed and based on the data, the 1a/9a and 3a/9a stx2/stx1 primer-probe combinations yielded the most consistently positive results. The Cts for the stx2 detection were very similar over the three stx2 primer concentrations tested (typically within one (1) Ct).

Further real-time PCR assays, similar to those described above, were run for the 1a/9a and 3a/9a combinations using the stx2 primers at 250 nM. The second set of assays varied the final concentration of the stx2 FAM detection probe: 200 nM, 300 nM, and 400 nM for each mix. Based on the results from these runs, subsequent assays utilized the stx2 detection probe at 250 nM for the 1a/9a combination and at 200 nM for the 3a/9a combination.

A third set of assays was performed, this time varying the stx1 forward and reverse primer final concentration at 200 nM, 300 nM, and 400 nM for each mix. Based on the results of this third set, subsequent assays utilized the stx1 primers at 400 nM for the 1a/9a combination and at 250 nM for the 3a/9a combination.

A fourth set of assays was performed, this time varying the stx1 probe final concentration at 200 nM, 300 nM, and 400 nM for each mix. Based on the data from this fourth set, 200 nM was selected as a suitable concentration for the stx1 detection probe.

Concluding Statements

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may be practiced in the absence of any element or elements, limitation or limitations, not specifically disclosed herein. Thus, for example, the terms "comprising," "including," containing," etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

What is claimed is:

1. A method for identifying a stx2 gene in a sample, said method comprising:
   a) contacting said sample with a pair of amplification oligomers comprising:
   (i) a first oligomer comprising a target hybridizing sequence consisting of SEQ ID NO: 33 and a second oligomer comprising a target hybridizing sequence consisting of SEQ ID NO: 34;
   (ii) a first oligomer comprising a target hybridizing sequence consisting of SEQ ID NO: 40 and a second oligomer comprising a target hybridizing sequence consisting of SEQ ID NO: 41; or
   (iii) a first oligomer comprising a target hybridizing sequence consisting of SEQ ID NO: 36 and a second oligomer comprising a target hybridizing sequence consisting of SEQ ID NO: 37;
   b) amplifying nucleic acid in said sample with said pair of amplification oligomers to obtain an amplification product; and
   c) determining the sequence of said amplification product or detecting said amplification product using a detection probe, wherein the pair of amplification oligomers have the property of amplifying the stx2 gene at a concentration below 7.5 copies/µl with no or very limited cross-reactivity.

2. The method of claim 1, wherein said sample comprises bacterial nucleic acid originating from *Escherichia coli*, *Citrobacter freundii*, *Aeromononas hydrophila*, *Aeromononas caviae*, or *Enterobacter cloacae*.

3. The method of claim 2, wherein said sample comprises bacterial nucleic acid originating from a strain of *Escherichia coli*.

4. The method of claim 3, wherein said strain of *Escherichia coli* is *E. coli* O157:H7.

5. The method of any one of claims 1-4, wherein said amplification step is performed using a polymerase chain reaction.

6. The method of claim 5, wherein said polymerase chain reaction is a real-time polymerase chain reaction.

7. The method of claim 1, wherein the detection probe is a fluorescence probe and is used to detect the amplification product in step c).

8. The method of claim 7, wherein the fluorescence probe comprises a fluorescent dye compound and a non-fluorescent quenching dye compound.

9. The method of claim 1, wherein said detection probe is an oligomer having a length of from about 15 to about 30 contiguous oligomer residues.

10. The method of claim 9, wherein
   for the amplification oligomer pair of (i), said probe has at least 90% sequence identity to SEQ ID NO:35;
   for the amplification oligomer pair of (ii), said probe has at least 90% sequence identity to SEQ ID NO:42;
   for the amplification oligomer pair of (iii), said probe has at least 90% sequence identity to SEQ ID NO: 39.

11. The method of claim 1, wherein step c) comprises determining the sequence of said amplification product by a sequencing reaction, a microarray, electrophoresis, or mass spectrometry.

12. A primer-probe set for identification of a stx2 gene, said primer-probe set comprising: a pair of amplification oligomers and an oligomer probe, said pair of amplification oligomers comprising:
   (i) a first oligomer comprising a target hybridizing sequence consisting of SEQ ID NO: 33 and a second oligomer comprising a target hybridizing sequence consisting of SEQ ID NO: 34;
   (ii) a first oligomer comprising a target hybridizing sequence consisting of SEQ ID NO: 40 and a second oligomer comprising a target hybridizing sequence consisting of SEQ ID NO: 41; or
   (iii) a first oligomer comprising a target hybridizing sequence consisting of SEQ ID NO: 36 and a second oligomer comprising a target hybridizing sequence consisting of SEQ ID NO: 37; and
   said oligomer probe hybridizable to a stx2 gene region located between the regions of hybridization of said pair of amplification oligomers, wherein the oligomer probe comprises a non-nucleotide detectable label, wherein the pair of amplification oligomers have the property of amplifying the stx2 gene at a concentration below 7.5 copies/µl with no or very limited cross-reactivity.

13. The primer-probe set of claim 12 wherein said probe has a length of from about 10 to about 40 contiguous oligomer residues.

14. The primer-probe set of claim 13 wherein
for the amplification oligomer pair of (i), said probe has at least 90% sequence identity to SEQ ID NO:35;
for the amplification oligomer pair of (ii), said probe has at least 90% sequence identity to SEQ ID NO:42; or
for the amplification oligomer pair of (iii), said probe has at least 90% sequence identity to SEQ ID NO: 39.

15. The primer-probe set of claim 14 further comprising an internal control system for verifying reaction conditions, said system comprising a control template polynucleotide, a pair of control amplification oligomers and a control probe.

16. A kit for identification of a stx2 gene, said kit comprising the primer-probe set of any one of claims 12 to 15 in combination with instructions for carrying out a polymerase chain reaction using said amplification oligomers.

17. The kit of claim 16, said kit further comprising a pair of stx1 amplification oligomers, each member of said pair of stx1 amplification oligomers having a length of from about 15 to about 25 contiguous nucleotides, said pair of stx1 amplification oligomers comprising:
(1-i) a first oligomer having at least 90% sequence identity to SEQ ID NO: 30 and a second oligomer having at least 90% sequence identity to SEQ ID NO: 31;
(1-ii) a first oligomer having at least 90% sequence identity to SEQ ID NO: 1 and a second oligomer having at least 90% sequence identity to SEQ ID NO: 2;
(1-iii) a first oligomer having at least 90% sequence identity to SEQ ID NO: 8 and a second oligomer having at least 90% sequence identity to SEQ ID NO: 9;
(1-iv) a first oligomer having at least 90% sequence identify to SEQ ID NO: 12 and a second oligomer having at least 90% sequence identity to SEQ ID NO: 13; or
(1-v) a first oligomer having at least 90% sequence identity to SEQ ID NO: 19 and a second oligomer having at least 90% sequence identity to SEQ ID NO: 20.

18. The kit of claim 16, further comprising a primer-probe set comprising a pair of stx1 amplification oligomers, each member of said pair of stx1 amplification oligomers having a length of from about 15 to about 25 contiguous nucleotides, said pair of stx1 amplification oligomers comprising:
(1-i) a first oligomer having at least 90% sequence identity to SEQ ID NO: 30 and a second oligomer having at least 90% sequence identity to SEQ ID NO: 31;
(1-ii) a first oligomer having at least 90% sequence identity to SEQ ID NO: 1 and a second oligomer having at least 90% sequence identity to SEQ ID NO: 2;
(1-iii) a first oligomer having at least 90% sequence identity to SEQ ID NO: 8 and a second oligomer having at least 90% sequence identity to SEQ ID NO: 9;
(1-iv) a first oligomer having at least 90% sequence identify to SEQ ID NO: 12 and a second oligomer having at least 90% sequence identity to SEQ ID NO: 13; or
(1-v) a first oligomer having at least 90% sequence identity to SEQ ID NO: 19 and a second oligomer having at least 90% sequence identity to SEQ ID NO: 20; and
an oligomer probe hybridizable to a stx1 gene region located between the regions of hybridization of said pair of stx1 amplification oligomers.

19. A composition comprising an amplification product for identification of a stx2 gene, said amplification product produced by the method of claim 1, and an oligomer probe hybridizable to the amplification product, wherein the oligomer probe comprises a non-nucleotide detectable label.

20. A composition comprising an amplicon generated using two primers that are specific for stx2 and an oligomer probe hybridizable to the amplicon, wherein the sequences of the two primers consist of one of the following pairs of SEQ ID NOs: 33 and 34; 36 and 37; or 40 and 41, wherein the amplicon is generated in an amplification reaction wherein stx2 is the target nucleic acid, and wherein the oligomer probe comprises a non-nucleotide detectable label.

21. The composition of claim 20, wherein the amplicon comprises a target sequence to which a probe comprising the sequence of any one of SEQ ID NOs: 35, 38, 39, 42, or 43 specifically hybridizes.

22. The method of claim 1, wherein part a) further comprises contacting said sample with a pair of stx1-specific amplification oligomers, each member of said stx1-specific pair of amplification oligomers having a length of from about 15 to about 25 contiguous nucleotides,
said pair of stx1-specific amplification oligomers selected from the group consisting of
(1-i) a first oligomer having at least 90% sequence identity to SEQ ID NO: 30 and a second oligomer having at least 90% sequence identity to SEQ ID NO: 31;
(1-ii) a first oligomer having at least 90% sequence identity to SEQ ID NO: 1 and a second oligomer having at least 90% sequence identity to SEQ ID NO: 2;
(1-iii) a first oligomer having at least 90% sequence identity to SEQ ID NO: 8 and a second oligomer having at least 90% sequence identity to SEQ ID NO: 9;
(1-iv) a first oligomer having at least 90% sequence identify to SEQ ID NO: 12 and a second oligomer having at least 90% sequence identity to SEQ ID NO: 13; and
(1-v) a first oligomer having at least 90% sequence identity to SEQ ID NO: 19 and a second oligomer having at least 90% sequence identity to SEQ ID NO: 20; and
part b) comprises amplifying nucleic acid in said sample with said pair of amplification oligomers and said stx1-specific pair of amplification oligomers to obtain at least one amplification product; and
part c) comprises determining the sequence of said at least one amplification product or detecting said at least one amplification product using the detection probe and a stx1-specific detection probe.

23. The method of claim 22, wherein each of the detection probe and the stx1-specific detection probe is an oligomer having a length of from about 15 to about 30 contiguous oligomer residues.

24. The method of claim 23, wherein
(I) for the amplification oligomer pair of (1-i), said stx1-specific probe has at least 90% sequence identity to SEQ ID NO:32;
for the amplification oligomer pair of (1-ii), said stx1-specific probe has at least 90% sequence identity to SEQ ID NO:5;
for the amplification oligomer pair of (1-iii), said stx1-specific probe has at least 90% sequence identity to SEQ ID NO: 11;
for the amplification oligomer pair of (1-iv), said stx1-specific probe has at least 90% sequence identity to SEQ ID NO:14; or
for the amplification oligomer pair of (1-v), said stx1-specific probe has at least 90% sequence identity to SEQ ID NO:22;
and
(II) for the amplification oligomer pair of (i), the detection probe has at least 90% sequence identity to SEQ ID NO:35;

for the amplification oligomer pair of (ii), the detection probe has at least 90% sequence identity to SEQ ID NO:42; or for the amplification oligomer pair of (iii), the detection probe has at least 90% sequence identity to SEQ ID NO: 39.

25. The method of any one of claims 22-24, wherein the pair of amplification oligomers and the stx1-specific pair of amplification oligomers are selected from the following combinations:
(A) the amplification oligomer pairs of (1-i) and (i);
(B) the amplification oligomer pairs of (1-i) and (ii);
(C) the amplification oligomer pairs of (1-ii) and (i); and
(D) the amplification oligomer pairs of (1-v) and (i).

26. The method of claim 25, wherein
for the combination of (A), the stx1-specific detection probe has at least 90% sequence identity to SEQ ID NO:32 and the detection probe has at least 90% sequence identity to SEQ ID NO:35;
for the combination of (B), the stx1-specific detection probe has at least 90% sequence identity to SEQ ID NO:32 and the detection probe has at least 90% sequence identity to SEQ ID NO:42;
for the combination of (C), the stx1-specific detection probe has at least 90% sequence identity to SEQ ID NO:5 and the detection probe has at least 90% sequence identity to SEQ ID NO:35; or
for the combination of (D), the stx1-specific detection probe has at least 90% sequence identity to SEQ ID NO:22 and the detection probe has at least 90% sequence identity to SEQ ID NO:35.

27. The method of claim 22, wherein said sample comprises bacterial nucleic acid originating from *Escherichia coli, Citrobacter freundii, Aeromononas hydrophila Aeromononas caviae,* or *Enterobacter cloacae.*

28. The method of claim 27, wherein said sample comprises bacterial nucleic acid originating from a strain of *Escherichia coli.*

29. The method of claim 28, wherein said strain of *Escherichia coli* is *E. coli* 0157:H7.

30. The method of claim 22, wherein said amplification step is performed using a polymerase chain reaction.

31. The method of claim 30, wherein said polymerase chain reaction is a real-time polymerase chain reaction.

32. The method of claim 22, wherein step c) comprises detecting said at least one amplification product using the detection probe and the stx1-specific detection probe.

33. The method of claim 32, wherein each of the detection probe and the stx1-specific detection probe is a fluorescence probe that comprises a fluorescent dye compound.

34. The method of claim 32, wherein each of the detection probe and the stx1-specific detection probe is a fluorescence probe that comprises a fluorescent dye compound and a non-fluorescent quenching dye compound.

35. A primer probe set comprising the primer probe set of claim 12, and further comprising a pair of stx1-specific amplification oligomers, each member of said stx1-specific pair of amplification oligomers having a length of from about 15 to about 25 contiguous nucleotides,
said pair of stx1-specific amplification oligomers selected from the group consisting of
(1-i) a first oligomer having at least 90% sequence identity to SEQ ID NO: 30 and a second oligomer having at least 90% sequence identity to SEQ ID NO: 31;
(1-ii) a first oligomer having at least 90% sequence identity to SEQ ID NO: 1 and a second oligomer having at least 90% sequence identity to SEQ ID NO: 2;
(1-iii) a first oligomer having at least 90% sequence identity to SEQ ID NO: 8 and a second oligomer having at least 90% sequence identity to SEQ ID NO: 9;
(1-iv) a first oligomer having at least 90% sequence identify to SEQ ID NO: 12 and a second oligomer having at least 90% sequence identity to SEQ ID NO: 13; and
(1-v) a first oligomer having at least 90% sequence identity to SEQ ID NO: 19 and a second oligomer having at least 90% sequence identity to SEQ ID NO: 20.

36. The primer probe set of claim 35, wherein the stx1-specific and stx2-specific pairs of amplification oligomers are selected from the following combinations of stx1-specific and stx2-specific oligomer pairs:
(A) the amplification oligomer pairs of (1-i) and (i);
(B) the amplification oligomer pairs of (1-i) and (ii);
(C) the amplification oligomer pairs of (1-ii) and (i); and
(D) the amplification oligomer pairs of (1-v) and (i).

37. The primer-probe set of claim 12, further comprising:
a pair of stx1-specific amplification oligomers, each member of said stx1-specific pair of amplification oligomers having a length of from about 15 to about 25 contiguous nucleotides, said pair of stx1-specific amplification oligomers selected from the group consisting of
(1-i) a first oligomer having at least 90% sequence identity to SEQ ID NO: 30 and a second oligomer having at least 90% sequence identity to SEQ ID NO: 31;
(1-ii) a first oligomer having at least 90% sequence identity to SEQ ID NO: 1 and a second oligomer having at least 90% sequence identity to SEQ ID NO: 2;
(1-iii) a first oligomer having at least 90% sequence identity to SEQ ID NO: 8 and a second oligomer having at least 90% sequence identity to SEQ ID NO: 9;
(1-iv) a first oligomer having at least 90% sequence identify to SEQ ID NO: 12 and a second oligomer having at least 90% sequence identity to SEQ ID NO: 13; and
(1-v) a first oligomer having at least 90% sequence identity to SEQ ID NO: 19 and a second oligomer having at least 90% sequence identity to SEQ ID NO: 20; and
a stx1-specific detection probe hybridizable to a stx1 gene region located between the regions of hybridization of said pair of stx1-specific amplification oligomers.

38. The primer-probe set of claim 37, wherein each of said stx1-specific detection probe and said oligomer probe hybridizable to a stx2 gene region is an oligomer having a length of from about 15 to about 30 or to about 40 contiguous oligomer residues.

39. The primer-probe set of claim 38, wherein
(I) for the amplification oligomer pair of (1-i), said stx1-specific probe has at least 90% sequence identity to SEQ ID NO:32;
for the amplification oligomer pair of (1-ii), said stx1-specific probe has at least 90% sequence identity to SEQ ID NO:5;
for the amplification oligomer pair of (1-iii), said stx1-specific probe has at least 90% sequence identity to SEQ ID NO: 11;
for the amplification oligomer pair of (1-iv), said stx1-specific probe has at least 90% sequence identity to SEQ ID NO:14; or
for the amplification oligomer pair of (1-v), said stx1-specific probe has at least 90% sequence identity to SEQ ID NO:22;
and
(II) for the amplification oligomer pair of (i), said oligomer probe hybridizable to a stx2 gene region has at least 90% sequence identity to SEQ ID NO:35;

for the amplification oligomer pair of (ii), said oligomer probe hybridizable to a stx2 gene region has at least 90% sequence identity to SEQ ID NO:42; or for the amplification oligomer pair of (iii), said oligomer probe hybridizable to a stx2 gene region has at least 90% sequence identity to SEQ ID NO: 39.

40. The primer-probe set of any one of claims 37-39, wherein the pair of amplification oligomers and the stx1-specific pair of amplification oligomers are selected from the following combinations of oligomer pairs:
(A) the amplification oligomer pairs of (1-i) and (i);
(B) the amplification oligomer pairs of (1-i) and (ii);
(C) the amplification oligomer pairs of (1-ii) and (i); and
(D) the amplification oligomer pairs of (1-v) and (i).

41. The primer-probe set of claim 40, wherein
for the combination of (A), the stx1-specific probe has at least 90% sequence identity to SEQ ID NO:32 and the oligomer probe hybridizable to a stx2 gene region has at least 90% sequence identity to SEQ ID NO:35;
for the combination of (B), the stx1-specific probe has at least 90% sequence identity to SEQ ID NO:32 and the oligomer probe hybridizable to a stx2 gene region has at least 90% sequence identity to SEQ ID NO:42;
for the combination of (C), the stx1-specific probe has at least 90% sequence identity to SEQ ID NO:5 and the oligomer probe hybridizable to a stx2 gene region has at least 90% sequence identity to SEQ ID NO:35; or
for the combination of (D), the stx1-specific probe has at least 90% sequence identity to SEQ ID NO:22 and the oligomer probe hybridizable to a stx2 gene region has at least 90% sequence identity to SEQ ID NO:35.

42. The primer-probe set of claim 37, further comprising an internal control system for verifying reaction conditions, said system comprising a control template polynucleotide, a pair of control amplification oligomers, and a control probe.

43. The primer-probe set of claim 42, wherein said pair of control amplification oligomers comprises a first oligomer having at least 90% sequence identity to SEQ ID NO:53 and a second oligomer having at least 90% sequence identity to SEQ ID NO:54.

44. The primer-probe set of claim 43, wherein said control probe is an oligomer having at least 90% sequence identity to SEQ ID NO:55.

45. A kit for amplification of at least one of a stx1 gene and a stx2 gene, said kit comprising the primer probe set of claim 36.

46. A kit for identification of at least one of a stx1 gene and a stx2 gene, said kit comprising the primer-probe set of any one of claims 37-39.

47. The kit of claim 18, wherein said oligomer probe hybridizable to the stx1 gene region has a length of from about 10 to about 40 contiguous oligomer residues.

48. The kit of claim 47, wherein
for the amplification oligomer pair of (1-i), said oligomer probe hybridizable to the stx1 gene region has at least 90% sequence identity to SEQ ID NO:32;
for the amplification oligomer pair of (1-ii), said oligomer probe hybridizable to the stx1 gene region has at least 90% sequence identity to SEQ ID NO:5;
for the amplification oligomer pair of (1-iii), said oligomer probe hybridizable to the stx1 gene region has at least 90% sequence identity to SEQ ID NO: 11;
for the amplification oligomer pair of (1-iv), said oligomer probe hybridizable to the stx1 gene region has at least 90% sequence identity to SEQ ID NO:14; or
for the amplification oligomer pair of (1-v), said oligomer probe hybridizable to the stx1 gene region has at least 90% sequence identity to SEQ ID NO:22.

49. The kit of claim 48, further comprising an internal control system for verifying reaction conditions, said system comprising a control template polynucleotide, a pair of control amplification oligomers and a control probe.

50. A primer-probe set for identification of a stx2 gene comprising a pair of amplification oligomers, said amplification oligomers comprising:
(i) a first oligomer consisting of the sequence of SEQ ID NO: 33 and a second oligomer consisting of the sequence of SEQ ID NO: 34;
(ii) a first oligomer consisting of the sequence of SEQ ID NO: 40 and a second oligomer consisting of the sequence of SEQ ID NO: 41; or
(iii) a first oligomer consisting of the sequence of SEQ ID NO: 36 and a second oligomer consisting of the sequence of SEQ ID NO: 37; and
an oligomer probe hybridizable to a stx2 gene region located between the regions of hybridization of said pair of amplification oligomers, wherein the oligomer probe comprises a non-nucleotide detectable label.

* * * * *

SEQUENCE LISTING

```
<160> NUMBER OF SEQ ID NOS: 57

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
tgacagtagc tataccacgt                                                  20

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2
agtgttgtac gaaatcccct                                                  20

<210> SEQ ID NO 3
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 3
atcagtcgta cggggatgca ga                                               22

<210> SEQ ID NO 4
<211> LENGTH: 23
<212> TYPE: DNA
<213> ORGANISM: Artificial Sequence
```

```
<220> FEATURE:
<223> OTHER INFORMATION: Synthetic Oligonucleotide

<400> SEQUENCE: 4
acagcgtgtt gcaggatca gtc                                              23

<210> SEQ ID NO 5
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 5
atgcagataa atcgccattc gttgac                                          26

<210> SEQ ID NO 6
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 6
ctatgcgaca ttaaatccag at                                              22

<210> SEQ ID NO 7
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 7
tagtcaacga atggcgattt atctgca                                         27

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 8
agacgtatgt agattcgctg                                                 20

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 9
tggatctatc cctctgacat                                                 20

<210> SEQ ID NO 10
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 10
atgtcattcg ctctgcaata ggtact                                          26
```

```
<210> SEQ ID NO 11
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 11
atcatcagta aagacgtacc tcctgat                                          27

<210> SEQ ID NO 12
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 12
gctgattttt cacatgttac ct                                               22

<210> SEQ ID NO 13
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 13
ctatgcgaca ttaaatccag at                                               22

<210> SEQ ID NO 14
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 14
ttgtctggtg acagtagcta taccac                                           26

<210> SEQ ID NO 15
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 15
aggggatttc gtacaacact                                                  20

<210> SEQ ID NO 16
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 16
aattcagtat taatgccacg ct                                               22

<210> SEQ ID NO 17
<211> LENGTH: 26
<212> TYPE: DNA
<213> ORGANISM: Artificial Sequence
<220> FEATURE:
<223> OTHER INFORMATION: Synthetic Oligonucleotide
```

```
<400> SEQUENCE: 17
acacgaacag agtcttgtcc atgata                                           26

<210> SEQ ID NO 18
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 18
atgatctcag tgggcgttct tatgta                                           26

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 19
agagcgatgt tacggtttgt                                                  20

<210> SEQ ID NO 20
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 20
atcaacatct tcagcagtca tt                                               22

<210> SEQ ID NO 21
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 21
agctgaagct ttacgttttc ggcaaat                                          27

<210> SEQ ID NO 22
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 22
cataagaacg cccactgaga tcatc                                            25

<210> SEQ ID NO 23
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 23
gaagctttac gttttcggca                                                  20
```

```
<210> SEQ ID NO 24
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 24
gaacagagtc ttgtccatga                                                 20

<210> SEQ ID NO 25
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 25
ctactcaacc ttccccagtt caatg                                           25

<210> SEQ ID NO 26
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 26 agagggatt tcgtacaaca ctgga                                            25

<210> SEQ ID NO 27
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 27
gtggcattaa tactgaattg tc                                              22

<210> SEQ ID NO 28
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 28
acaatatttt attgtgcgta atcc                                            24

<210> SEQ ID NO 29
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 29
atcatgcatc gcgagttgcc agaa                                            24

<210> SEQ ID NO 30
<211> LENGTH: 22
<212> TYPE: DNA
<213> ORGANISM: Artificial Sequence
<220> FEATURE:
<223> OTHER INFORMATION: Synthetic Oligonucleotide
```

```
<400> SEQUENCE: 30
cgataccttt acagttaaag tg                                              22

<210> SEQ ID NO 31
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 31
tccattatga caggcattag tt                                              22

<210> SEQ ID NO 32
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 32
atggaatctt cagtctcttc ttctcagt                                        28

<210> SEQ ID NO 33
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 33
gggtactgtg cctgttac                                                   18

<210> SEQ ID NO 34
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 34
gtccgtatac tatttaacga ag                                              22

<210> SEQ ID NO 35
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 35
ttcttcggta tcctattccc ggga                                            24

<210> SEQ ID NO 36
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 36
catgacaacg gacagcag                                                   18
```

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 37
ctccattaac gccagatatg                                              20

<210> SEQ ID NO 38
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 38
accagtgagt gacgactgat ttgcat                                       26

<210> SEQ ID NO 39
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 39
ataccactct gcaacgtgtc gca                                          23

<210> SEQ ID NO 40
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 40
cagagatgca tccagagc                                                18

<210> SEQ ID NO 41
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 41
ccggaagcac attgctga                                                18

<210> SEQ ID NO 42
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 42
cagagagaat tcgtcaggc actg                                          24

<210> SEQ ID NO 43
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 43
acaggagcag tttcagacag tgc                                              23

<210> SEQ ID NO 44
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 44
ggacctcact ctgaactg                                                    18

<210> SEQ ID NO 45
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 45
tattattaaa ggatattctc ccca                                             24

<210> SEQ ID NO 46
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 46
tcagcaatgt gcttccggag tatc                                             24

<210> SEQ ID NO 47
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 47
gaatgtcaga taagtggcga                                                  20

<210> SEQ ID NO 48
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 48
ccgccattgc attaacagaa                                                  20

<210> SEQ ID NO 49
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 49
tgcaaataaa accgccataa acatcttct                                        29

```
<210> SEQ ID NO 50
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 50
caggagcgta ggaataccat c                                             21

<210> SEQ ID NO 51
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 51
gggctaactg tgaagattca atag                                          24

<210> SEQ ID NO 52
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 52
tcactgattc aagcacgtta gaaggcca                                      28

<210> SEQ ID NO 53
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 53
gagttggtaa acagatcatg c                                             21

<210> SEQ ID NO 54
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 54
gacttgtggc cttctaacg                                                19

<210> SEQ ID NO 55
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 55
tatcgagcac aggagcgtag gaata                                         25

<210> SEQ ID NO 56
<211> LENGTH: 1230
<212> TYPE: DNA
<213> ORGANISM: Escherichia coli
```

<300> PUBLICATION INFORMATION:
<308> DATABASE ACCESSION NUMBER: GB Acc. No. BA000007; gi:47118301;
    bases 2924490 to 2925719
<309> DATABASE ENTRY DATE: 2008-01-18
<313> RELEVANT RESIDUES IN SEQ ID NO: (1)..(1230)

<400> SEQUENCE: 56

```
aatatgaaaa taattatttt tagagtgcta acttttttct ttgttatctt ttcagttaat      60
gtggttgcga aggaatttac cttagacttc tcgactgcaa agacgtatgt agattcgctg     120
aatgtcattc gctctgcaat aggtactcca ttacagacta tttcatcagg aggtacgtct     180
ttactgatga ttgatagtgg cacaggggat aatttgtttg cagttgatgt cagagggata     240
gatccagagg aagggcggtt taataatcta cggcttattg ttgaacgaaa taatttatat     300
gtgacaggat tgttaacag acaaataat gttttttatc gctttgctga ttttcacat      360
gttacctttc caggtacaac agcggttaca ttgtctggtg acagtagcta taccacgtta     420
cagcgtgttg cagggatcag tcgtacgggg atgcagataa atcgccattc gttgactact     480
tcttatctgg atttaatgtc gcatagtgga acctcactga cgcagtctgt ggcaagagcg     540
atgttacggt tgttactgt gacagctgaa gctttacgtt tcggcaaat acagagggga     600
tttcgtacaa cactggatga tctcagtggg cgttcttatg taatgactgc tgaagatgtt     660
gatcttacat tgaactgggg aaggttgagt agtgtcctgc ctgattatca tggacaagac     720
tctgttcgtg taggaagaat ttcttttgga agcattaatg caattctggg aagcgtggca     780
ttaatactga attgtcatca tcatgcatcg cgagttgcca gaatggcatc tgatgagttt     840
ccttctatgt gtccggcaga tggaagagtc cgtgggatta cgcacaataa aatattgtgg     900
gattcatcca ctctggggcg aattctgatg cgcagaacta ttagcagttg agggggtaaa     960
atgaaaaaaa cattattaat agctgcatcg ctttcatttt tttcagcaag tgcgctggcg    1020
acgcctgatt gtgtaactgg aaaggtggag tatacaaat ataatgatga cgatacctt     1080
acagttaaag tgggtgataa agaattattt accaacagat ggaatcttca gtctcttctt    1140
ctcagtgcgc aaaattacggg gatgactgta accattaaaa ctaatgcctg tcataatgga    1200
gggggattca gcgaagttat ttttcgttga                                     1230
```

<210> SEQ ID NO 57
<211> LENGTH: 1241
<212> TYPE: DNA
<213> ORGANISM: Escherichia coli
<300> PUBLICATION INFORMATION:
<308> DATABASE ACCESSION NUMBER: GB Acc. No. BA000007; gi:47118301;
    bases 1266965 to 1268205
<309> DATABASE ENTRY DATE: 2008-01-18
<313> RELEVANT RESIDUES IN SEQ ID NO: (1)..(1241)

<400> SEQUENCE: 57

```
atgaagtgta tattatttaa atgggtactg tgcctgttac tgggttttc ttcggtatcc      60
tattcccggg agtttacgat agactttcg acccaacaaa gttatgtctc ttcgttaaat     120
agtatacgga cagagatatc gacccctctt gaacatatat ctcaggggac cacatcggtg    180
tctgttatta accacacccc accgggcagt tattttgctg tggatatacg agggcttgat    240
gtctatcagg cgcgttttga ccatcttcgt ctgattattg agcaaaataa tttatatgtg    300
gccgggttcg ttaatacggc aacaaatact ttctaccgtt tttcagattt tacacatata    360
tcagtgcccg gtgtgacaac ggtttccatg acaacggaca gcagtatac cactctgcaa    420
cgtgtcgcag cgctggaacg ttccggaatg caaatcagtc gtcactcact ggtttcatca    480
```

-continued

```
tatctggcgt taatggagtt cagtggtaat acaatgacca gagatgcatc cagagcagtt    540
ctgcgttttg tcactgtcac agcagaagcc ttacgcttca ggcagataca gagagaattt    600
cgtcaggcac tgtctgaaac tgctcctgtg tatacgatga cgccgggaga cgtggacctc    660
actctgaact gggggcgaat cagcaatgtg cttccggagt atcggggaga ggatggtgtc    720
agagtgggga gaatatcctt taataatata tcagcgatac tggggactgt ggccgttata    780
ctgaattgcc atcatcaggg ggcgcgttct gttcgcgccg tgaatgaaga gagtcaacca    840
gaatgtcaga taactggcga caggcctgtt ataaaaataa acaatacatt atgggaaagt    900
aatacagctg cagcgtttct gaacagaaag tcacagtttt tatatacaac gggtaaataa    960
aggagttaag catgaagaag atgtttatgg cggttttatt tgcattagct tctgttaatg   1020
caatggcggc ggattgtgct aaaggtaaaa ttgagttttc caagtataat gaggatgaca   1080
catttacagt gaaggttgac gggaaagaat actggaccag tcgctggaat ctgcaaccgt   1140
tactgcaaag tgctcagttg acaggaatga ctgtcacaat caaatccagt acctgtgaat   1200
caggctccgg atttgctgaa gtgcagttta ataatgactg a                       1241
```